(12) United States Patent
Saito et al.

(10) Patent No.: US 9,532,740 B2
(45) Date of Patent: Jan. 3, 2017

(54) ENDOSCOPE SYSTEM, PROCESSING APPARATUS FOR THE SAME, AND IMAGE GENERATING METHOD

(71) Applicant: FUJIFILM Corporation, Tokyo (JP)

(72) Inventors: Takaaki Saito, Ashigarakami-gun (JP); Hiroshi Yamaguchi, Ashigarakami-gun (JP); Takayuki Iida, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 321 days.

(21) Appl. No.: 14/196,625

(22) Filed: Mar. 4, 2014

(65) Prior Publication Data

US 2014/0187881 A1 Jul. 3, 2014

Related U.S. Application Data

(63) Continuation of application No. PCT/JP2012/071174, filed on Aug. 22, 2012.

(30) Foreign Application Priority Data

Sep. 5, 2011 (JP) ................................ 2011-193186

(51) Int. Cl.
*A61B 5/1455* (2006.01)
*A61B 1/00* (2006.01)
(Continued)

(52) U.S. Cl.
CPC ......... *A61B 5/14552* (2013.01); *A61B 1/0005* (2013.01); *A61B 1/00009* (2013.01);
(Continued)

(58) Field of Classification Search
None
See application file for complete search history.

(56) References Cited

U.S. PATENT DOCUMENTS

2002/0168096 A1 11/2002 Hakamata et al.
2003/0176768 A1 9/2003 Gono et al.
(Continued)

FOREIGN PATENT DOCUMENTS

EP 2 305 094 A1 4/2011
JP 2648494 B2 8/1997
(Continued)

OTHER PUBLICATIONS

International Search Report, issued in PCT/JP2012/071174, dated Oct. 23, 2012.
(Continued)

*Primary Examiner* — Eric Winakur
*Assistant Examiner* — Marjan Fardanesh
(74) *Attorney, Agent, or Firm* — Birch, Stewart, Kolasch & Birch, LLP

(57) ABSTRACT

An oxygen saturation level of hemoglobin in blood is correctly acquired without lowering a frame rate. A subject body illuminated with white light W is imaged by a color CCD to obtain signals Bs1, Gs1 and Rs1. The subject body is illuminated with blue narrow band light BN of which absorption coefficient is changed by a change in the oxygen saturation level of the hemoglobin in blood, and imaged by the color CCD to obtain signals Bs2, Gs2 and Rs2. The signal Bs2 is divided by the signal Gs1 to determine a normalized signal Bs2/Gs1. The oxygen saturation level of blood vessels of the surface of body tissue is obtained according to the normalized signal Bs2/Gs1. The oxygen saturation level is visualized in a pseudo color, to form an oxygen saturation level image.

14 Claims, 20 Drawing Sheets

(51) Int. Cl.
*A61B 1/06* (2006.01)
*A61B 5/1459* (2006.01)
*G06T 7/00* (2006.01)
*A61B 5/00* (2006.01)

(52) U.S. Cl.
CPC .......... *A61B 1/0638* (2013.01); *A61B 5/1459* (2013.01); *A61B 5/14551* (2013.01); *G06T 7/0012* (2013.01); *A61B 1/0653* (2013.01); *A61B 5/489* (2013.01); *G06T 2207/10016* (2013.01); *G06T 2207/10024* (2013.01); *G06T 2207/10068* (2013.01); *G06T 2207/10152* (2013.01); *G06T 2207/20212* (2013.01); *G06T 2207/30101* (2013.01)

(56) References Cited

U.S. PATENT DOCUMENTS

| | | | |
|---|---|---|---|
| 2005/0020926 A1* | 1/2005 | Wiklof | A61B 1/00193 600/476 |
| 2006/0113298 A1* | 6/2006 | Nishizawa | A61B 18/18 219/679 |
| 2010/0103250 A1 | 4/2010 | Ishihara | |
| 2011/0077462 A1 | 3/2011 | Saitou et al. | |

FOREIGN PATENT DOCUMENTS

| | | |
|---|---|---|
| JP | 2002-34893 A | 2/2002 |
| JP | 2002-336187 A | 11/2002 |
| JP | 2003-36436 A | 2/2003 |
| JP | 2008-183349 A | 8/2008 |

OTHER PUBLICATIONS

Written Opinion of the International Searching Authority, issued in PCT/JP2012/071174, dated Oct. 23, 2012.
Extended European Search Report dated Apr. 24, 2015, issued in European Patent Application No. 12829931.0.
International Preliminary Report on Patentability and English translation of the Written Opinion of the International Searching Authority (Forms PCT/IB/338, PCT/IB/373 and PCT/ISA/237), dated Mar. 20, 2014, for corresponding International Application No. PCT/JP2012/071174.
Chinese Office Action and Search Report, issued Jul. 28, 2015, for Chinese Application No. 201280043124.7, along with an English translation of the Chinese Office Action.

\* cited by examiner

F I G . 4
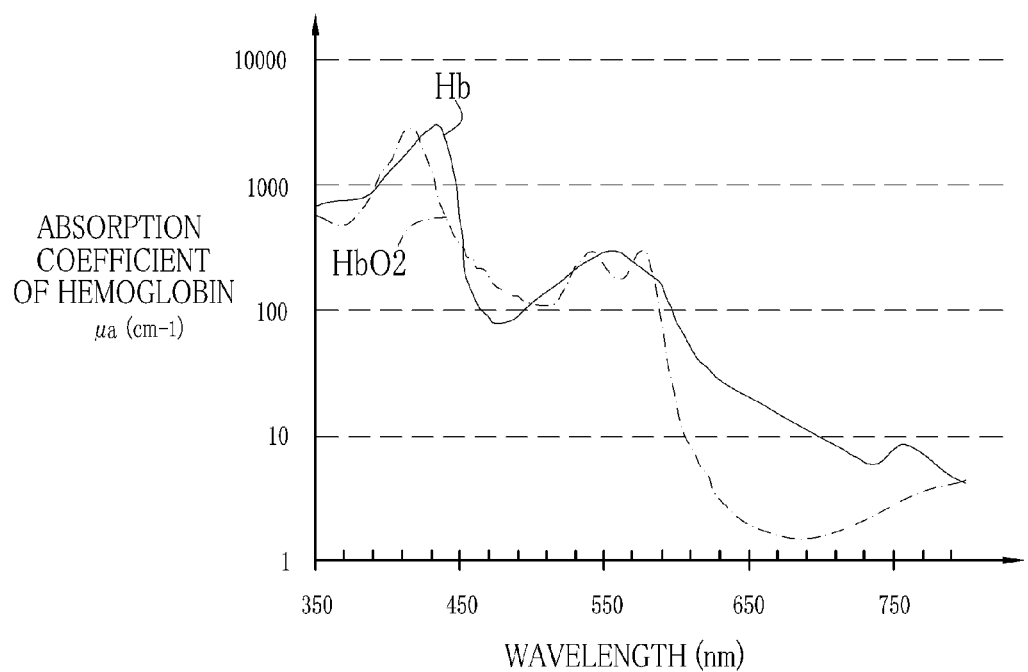
F I G . 5
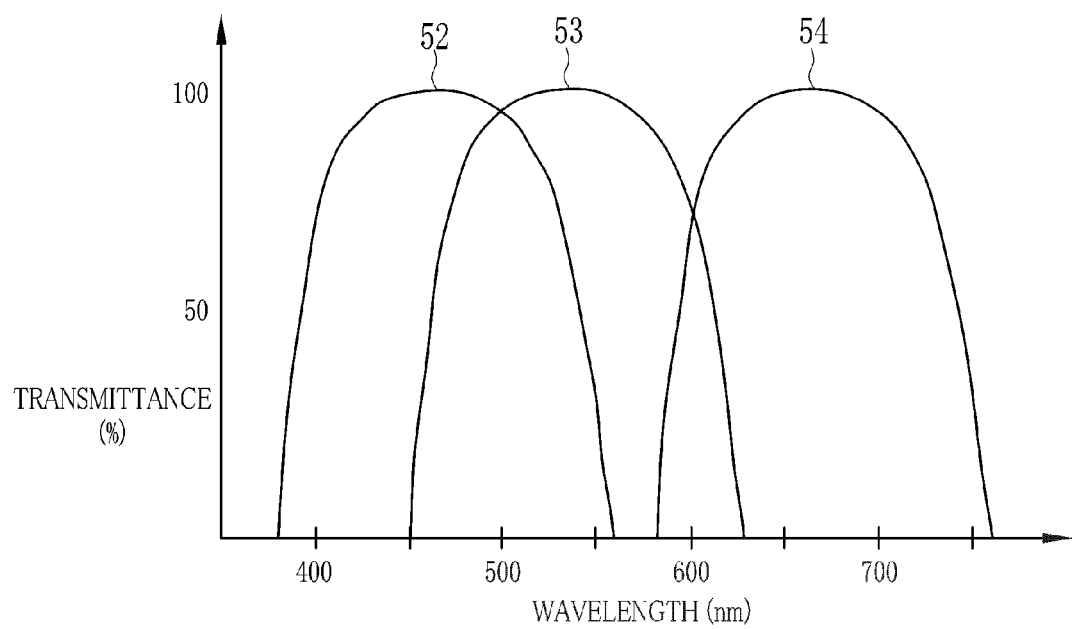

| NORMALIZED SIGNAL | O2 SATURATION LEVEL (%) |
|---|---|
| a1~a2 | S1 |
| a2~a3 | S2 |
| ⋮ | ⋮ |
| a(n-1)~an | Sn |

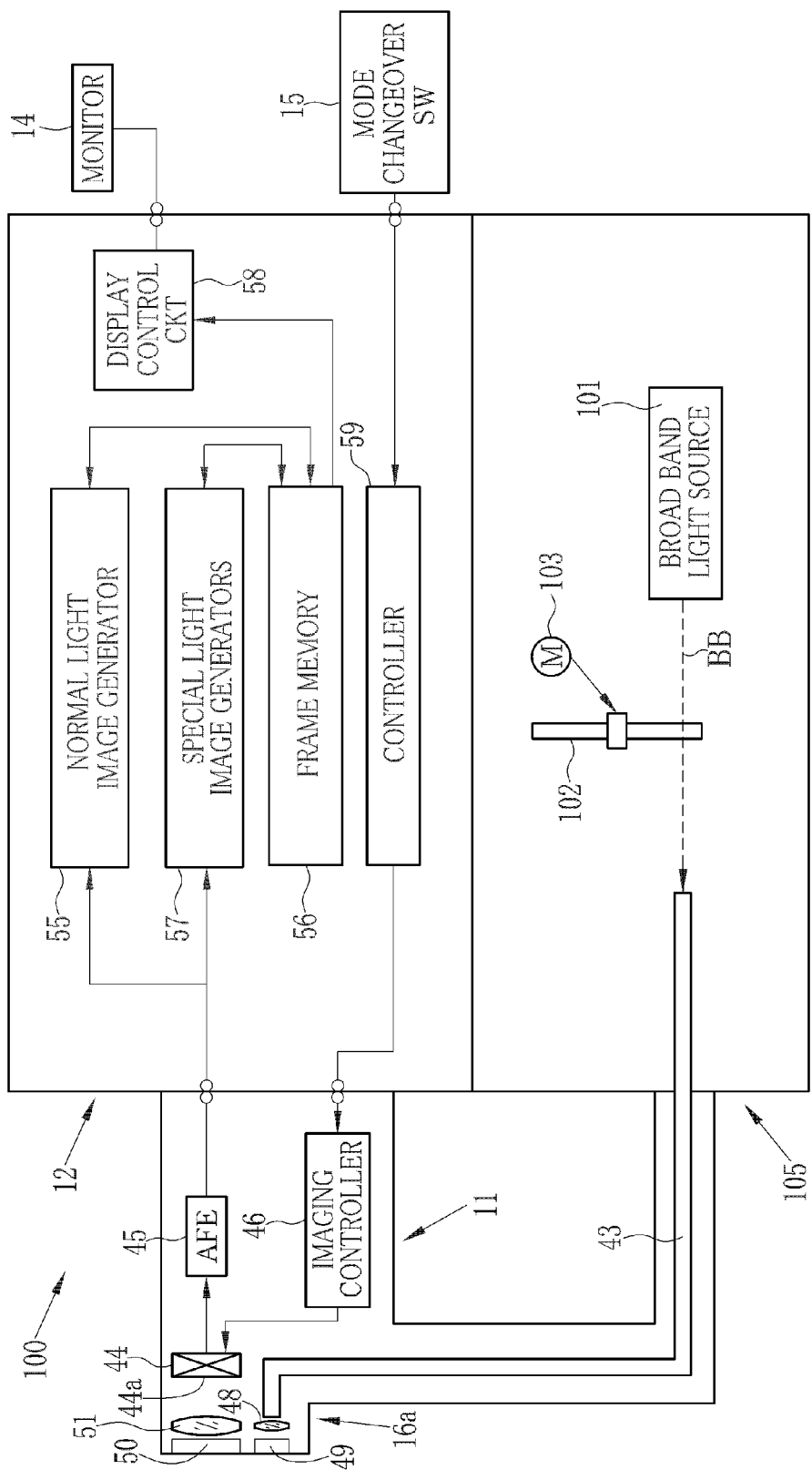
F I G. 18

ENDOSCOPE SYSTEM, PROCESSING APPARATUS FOR THE SAME, AND IMAGE GENERATING METHOD

CROSS REFERENCE TO RELATED APPLICATIONS

This non-provisional application is a Continuation of International Application No. PCT/JP2012/071174 filed on Aug. 22, 2012, which claims the benefit of Japanese Application No. 2011-193186 filed in Japan on Sep. 5, 2011. The entire contents of all of the above applications are hereby incorporated by reference.

BACKGROUND OF THE INVENTION

1. Field of the Invention

The present invention relates to an endoscope system, processing apparatus for the same, and image generating method in which body function information such as an oxygen saturation level is visualized.

2. Description Related to the Prior Art

Recently in the medicine, an endoscope system including an illuminator, endoscope apparatus and processing apparatus has been used widely. In an endoscopic diagnosis with the endoscope system, normal light imaging is carried out by use of white light or broad band light as illuminating light. Also, special light imaging is carried out by use of narrow band light of which a range of a wavelength is made narrow as disclosed in JP-B 2648494.

In JP-B 2648494, information related to an oxygen saturation level of hemoglobin in blood from an image signal obtained by imaging a subject body is acquired by use of light absorption characteristic of blood vessels or scattering characteristic of body tissue. The information is visualized in a pseudo color image, to form an oxygen saturation level image. Thus, discovery of a cancer of which the oxygen saturation level is characteristically low can be facilitated by use of the oxygen saturation level image for diagnosis. Performance in the diagnosis can be higher.

According to JP-B 2648494, image information of two wavelengths are acquired, including a first wavelength component of which an absorption coefficient of oxyhemoglobin is larger than the absorption coefficient of deoxyhemoglobin, and a second wavelength component of which the absorption coefficient of the deoxyhemoglobin is larger than the absorption coefficient of the oxyhemoglobin. A relationship of largeness and smallness of the absorption coefficient of the oxyhemoglobin and the absorption coefficient of the deoxyhemoglobin is different between the first and second wavelength components. Thus, a difference in a pixel value between the value of the image information of the two wavelengths is changed largely by a change in the oxygen saturation level. A change in the difference in the pixel value is indicated as a color difference on the oxygen saturation level image. It is possible to understand an oxygen condition of blood vessels according to the color difference.

Also, in JP-B 2648494, third image information having components of an equal absorption wavelength range where the absorption coefficient of the oxyhemoglobin is equal to the absorption coefficient of the deoxyhemoglobin is acquired for comparing the pixel value of first image information including a first wavelength component and second image information including a second wavelength component. Accordingly, the image information of three frames is acquired for the purpose of forming the oxygen saturation level image of one frame in JP-B 2648494. It is likely that a frame rate is lower and followability of a motion image may be dropped upon occurrence of movement with a subject body.

SUMMARY OF THE INVENTION

In view of the foregoing problems, an object of the present invention is to provide an endoscope system, processing apparatus for the same, and image generating method in which a frame rate will not be lowered and an oxygen saturation level of hemoglobin in blood can be correctly indicated.

In order to achieve the above and other objects and advantages of this invention, an endoscope system includes an illuminator for irradiating light to a subject body. There is an image signal acquisition device for imaging of a reflection image of the subject body illuminated with the light, to acquire a first image signal according to first reflected light having a first wavelength range and having an absorption coefficient changeable with an oxygen saturation level of hemoglobin in blood, and to acquire a second image signal according to second reflected light having a second wavelength range different from the first wavelength range. A normalized signal forming device normalizes the first image signal by use of the second image signal to form a normalized signal. An image generator generates an oxygen saturation level image by visualizing the oxygen saturation level of a blood vessel present at a particular depth according to the normalized signal. A display displays the oxygen saturation level image.

Preferably, the image signal acquisition device acquires a third image signal according to reflected light of white light by imaging the subject body illuminated with the white light. The image generator generates a first oxygen saturation level image in which a blood vessel with a lower value of the oxygen saturation level than a reference value is expressed in a pseudo color according to the normalized signal and the third image signal.

Preferably, the image generator includes a first memory for previously storing a relationship between the normalized signal and the oxygen saturation level. An oxygen saturation level acquisition device acquires the oxygen saturation level from the normalized signal according to the relationship from the first memory. An oxygen saturation level image generating device generates the first oxygen saturation level image according to the oxygen saturation level and the third image signal.

Preferably, the image generator includes a blood vessel enhanced image generating device for generating a blood vessel enhanced image in which the blood vessel at the particular depth is enhanced according to the third image signal. The oxygen saturation level image generating device generates the first oxygen saturation level image by considering information of the oxygen saturation level with the blood vessel enhanced image.

Preferably, furthermore, a normal light image generator generates a normal light image according to the third image signal. A blood vessel extraction device creates a blood vessel extraction image in which the blood vessel at the particular depth is extracted from the normal light image. The blood vessel enhanced image generating device generates the blood vessel enhanced image by combining the blood vessel extraction image with the normal light image.

Preferably, the blood vessel extraction device extracts the blood vessel at the particular depth from the normal light image according to a ratio between blue and green signals in the normal light image.

In another preferred embodiment, the image generator includes a second memory for previously storing a relationship between the normalized signal and a gain for changing a signal value of the third image signal. A gain acquisition device acquires the gain from the normalized signal according to the relationship from the second memory. An oxygen saturation level image generating device generates the oxygen saturation level image by changing the signal value of the third image signal according to the gain.

Preferably, the image generator generates a second oxygen saturation level image according to the normalized signal in such a form that a blood vessel and a portion different from the blood vessel are expressed in a pseudo color and that a color of the blood vessel is changed according to the oxygen saturation level.

Preferably, furthermore, a controller controls the illuminator or the image signal acquisition device to set a signal ratio between the first and second image signals at a predetermined value.

Preferably, the illuminator includes a first semiconductor light source for emitting first light with the first wavelength range. A second semiconductor light source emits second light with the second wavelength range.

In still another preferred embodiment, the illuminator includes a first semiconductor light source for emitting first light with the first wavelength range. A wavelength separator creates second light with the second wavelength range by wavelength separation of white light.

Preferably, assuming that the particular depth is a depth of surface tissue, the first wavelength range is 460-480 nm, and assuming that the particular depth is a depth of intermediate or deep tissue, the first wavelength range is 640-660 nm.

Also, a processing apparatus for an endoscope system is provided, and includes a receiver for receiving first and second image signals from an electronic endoscope, the electronic endoscope including an image signal acquisition device for imaging of a reflection image of a subject body illuminated with light, to acquire the first image signal according to first reflected light having a first wavelength range and having an absorption coefficient changeable with an oxygen saturation level of hemoglobin in blood, and to acquire the second image signal according to second reflected light having a second wavelength range different from the first wavelength range. A normalized signal forming device normalizes the first image signal by use of the second image signal to form a normalized signal. An image generator generates an oxygen saturation level image by visualizing the oxygen saturation level of a blood vessel present at a particular depth according to the normalized signal.

Also, an image generating method is provided, and includes an illuminating step of irradiating light to a subject body. In an image signal acquiring step, there is imaging of a reflection image of the subject body illuminated with the light, to acquire a first image signal according to first reflected light having a first wavelength range and having an absorption coefficient changeable with an oxygen saturation level of hemoglobin in blood, and to acquire a second image signal according to second reflected light having a second wavelength range different from the first wavelength range. In a normalized signal forming step, the first image signal is normalized by use of the second image signal to form a normalized signal. In an oxygen saturation level image generating step, an oxygen saturation level image is generated by visualizing the oxygen saturation level of a blood vessel present at a particular depth according to the normalized signal.

According to the present invention, an oxygen saturation level of a blood vessel positioned at a depth where light of a first wavelength range is passage in a subject body according to image signals of two wavelengths, and visualized, the image signals including a first image signal according to first reflected light having the first wavelength range and having an absorption coefficient changeable with an oxygen saturation level of hemoglobin in blood, and a second image signal according to second reflected light having a second wavelength range different from the first wavelength range. Therefore, it is possible to acquire and visualize the oxygen saturation level without lowering a frame rate, because of a decrease by one wavelength in comparison with the construction of the prior document. The oxygen saturation level can be determined correctly by normalizing the first image signal with the second image signal.

BRIEF DESCRIPTION OF THE DRAWINGS

The above objects and advantages of the present invention will become more apparent from the following detailed description when read in connection with the accompanying drawings, in which:

FIG. 4 is a graph illustrating an absorption coefficient of hemoglobin;

FIG. 5 is a graph illustrating a spectral transmittance of R, G and B color filters;

FIG. 13 is a view illustrating an oxygen saturation table;

FIG. 18 is a schematic view illustrating an endoscope system of a second embodiment;

DETAILED DESCRIPTION OF THE PREFERRED EMBODIMENT(S) OF THE PRESENT INVENTION

Figure 1:
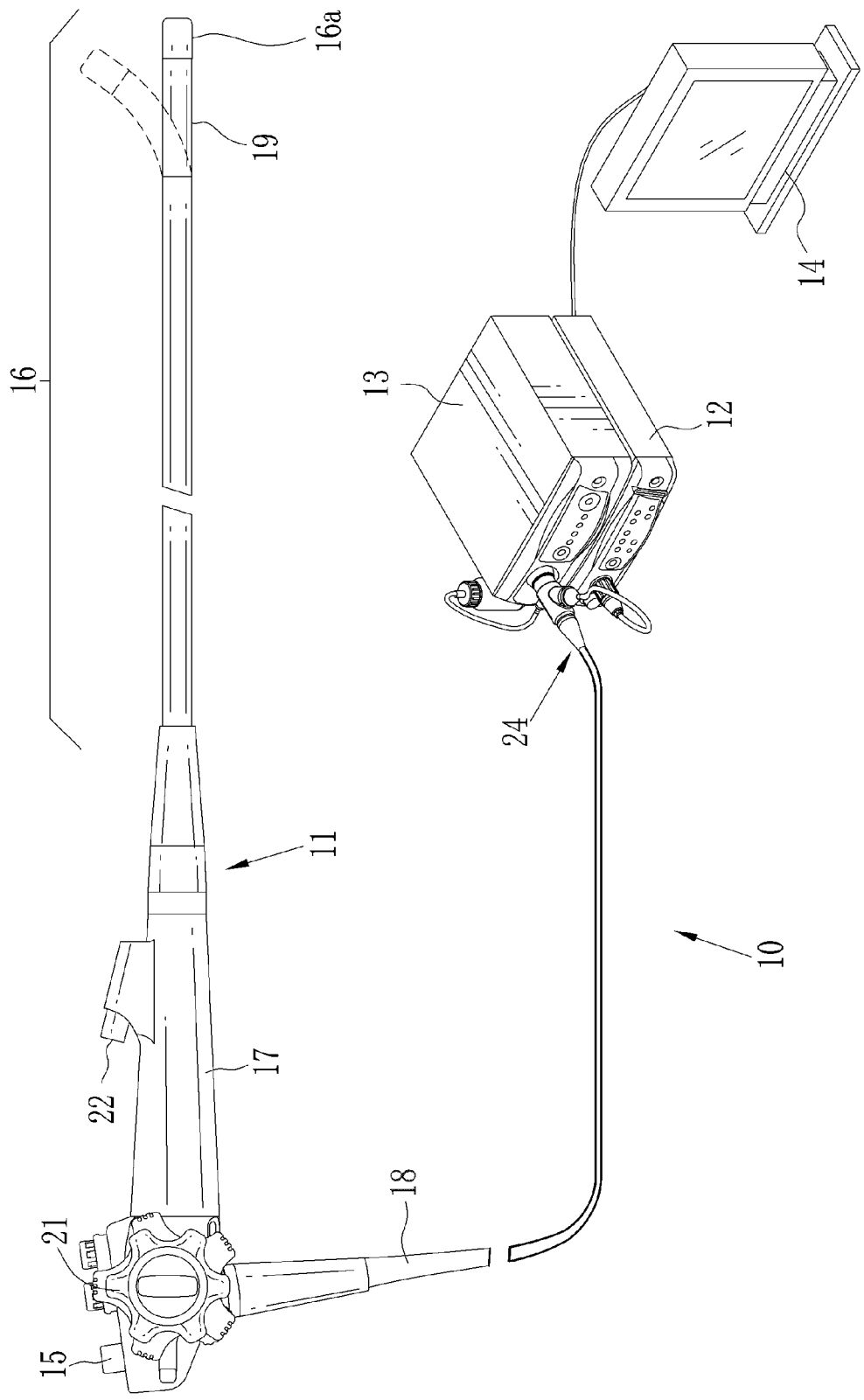
FIG. 1 is an external view illustrating an endoscope system.

As illustrated in FIG. 1, an endoscope system 10 of a first embodiment includes an electronic endoscope 11, a processing apparatus 12, an illuminator 13 and a monitor 14 (display). The electronic endoscope 11 images an inside of a subject body. The processing apparatus 12 generates an image according to a signal from the electronic endoscope, and carries out image processing of various functions. The illuminator 13 emits light for lighting the subject body. The monitor 14 displays an endoscopic image.

There are a normal imaging mode, a surface imaging mode and an intermediate and deep imaging mode in the endoscope system 10, which in the normal imaging mode, displays a normal light image on the monitor 14 after imaging a subject body illuminated by white light, and in the surface imaging mode, displays an oxygen saturation level image on the monitor 14 after visualizing an oxygen saturation level of superficial blood vessels, and in the intermediate and deep imaging mode, displays an oxygen saturation level image on the monitor 14 after visualizing an oxygen saturation level of intermediate and deep blood vessels. Those modes are changed over by a mode changeover SW 15.

The electronic endoscope 11 includes a flexible elongated tube 16, a handle 17 and a universal cable 18, the elongated tube 16 being entered in a body cavity, the handle 17 being disposed at a proximal end portion of the elongated tube 16, the universal cable 18 connecting the handle 17 to the processing apparatus 12 and the illuminator 13. A steering device 19 is formed with a distal end of the elongated tube 16 and has a plurality of link elements connected to one another. The steering device 19 is steered in operation in upper and lower directions and right and left directions by manipulating angle adjusting wheels 21 on the handle. A tip device 16a is provided at a distal end of the steering device 19, and contains an optical system and the like for internal imaging in a body cavity. The tip device 16a is directed in a desired direction in the body cavity by steering operation of the steering device 19.

A connector 24 is coupled with the universal cable 18. The connector 24 is a composite type of connector including a communication connector and a light source connector. The electronic endoscope 11 is connected by the connector 24 to the processing apparatus 12 and the illuminator 13 in a removable manner.

Figure 2:
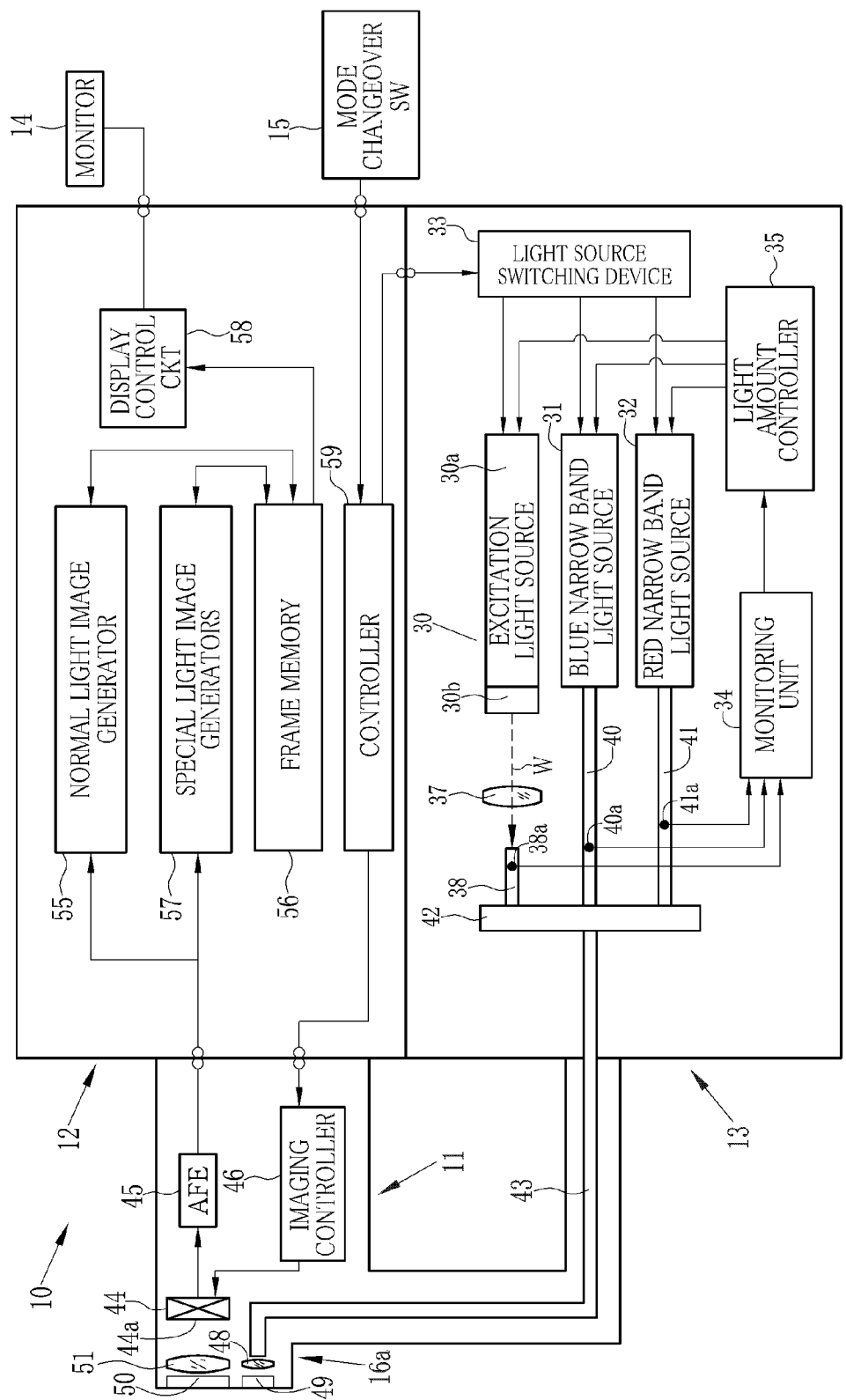
FIG. 2 is a schematic view illustrating the endoscope system of a first embodiment.

As illustrated in FIG. 2, the illuminator 13 includes a white light source unit 30, a blue narrow band light source 31, a red narrow band light source 32, a light source switching device 33, a monitoring unit 34 and a light amount controller 35, the white light source unit 30 emitting white light W, the blue narrow band light source 31 emitting blue narrow band light BN, the red narrow band light source 32 emitting red narrow band light RN, the light source switching device 33 switching on and off those light sources 30, 31 and 32, the monitoring unit 34 monitoring light amounts of the white light W, blue narrow band light BN and red narrow band light RN, the light amount controller 35 controlling the light amounts by controlling driving of the white light source unit 30, the blue narrow band light source 31 and the red narrow band light source 32.

The white light source unit 30 includes an excitation light source 30a for emitting excitation light, and phosphor 30b for emitting luminescence in response to the excitation light. The excitation light source 30a is constituted by a semiconductor light source such as a laser diode and the like. The phosphor 30b is constituted by plural phosphor substances (for example, phosphor substances such as YAG phosphor substance and BAM phosphor substance ($BaNgAl_{10}O_{17}$)) for excitation of emission from green to red by partially absorbing the excitation light. The excited light (fluorescence) of emission from green to red from the phosphor 30b is combined with the excitation light passed through the phosphor 30b without absorption, to generate white light W. The generated white light W passes through a condensing lens 37 and enters a white light optical fiber 38.

The blue narrow band light source 31 is constituted by a semiconductor light source such as a laser diode, and emits blue narrow band light BN of which a blue wavelength band is limited to a particular wavelength band. The blue narrow band light BN enters a blue narrow band light optical fiber 40. The red narrow band light source 32 is constituted by a semiconductor light source such as a laser diode in a manner similar to the blue narrow band light source 31, and emits red narrow band light RN of which a red wavelength band is limited to a particular wavelength band. The red narrow band light RN enters a red narrow band light optical fiber 41.

The light amount controller 35 is connected to the excitation light source 30a, the blue narrow band light source 31 and the red narrow band light source 32, and adjusts light amounts of excitation light, blue narrow band light BN and red narrow band light RN in constant ranges. As the excitation light is adjusted by the light amount controller 35, the light amount of the white light W is adjusted.

A coupler 42 optically couples a light guide 43 in the electronic endoscope to the white light optical fiber 38, the blue narrow band light optical fiber 40 and the red narrow band light optical fiber 41. This makes it possible to travel the white light W, blue narrow band light BN and red narrow band light RN into the light guide 43.

The light source switching device 33 is connected to a controller 59 in the processing apparatus, and changes over the excitation light source 30a, the blue narrow band light source 31 and the red narrow band light source 32 to a turn-on state (switched on) or a turn-off state (switched off) according to command from the controller 59. While the normal imaging mode is set in the first embodiment, the excitation light source 30a is always turned on, and the blue narrow band light source 31 and the red narrow band light source 32 are always turned off. Thus, only the white light W is irradiated to the subject body.

Also, while the surface imaging mode is set, the excitation light source 30a and the blue narrow band light source 31 are turned on alternately, to irradiate the white light W and blue narrow band light BN to an imaging area alternately. While the intermediate and deep imaging mode is set, the excitation light source 30a and the red narrow band light source 32 are turned on alternately, to irradiate the white light W and red narrow band light RN to the imaging area alternately.

The monitoring unit 34 monitors the light amounts of the white light W, blue narrow band light BN and red narrow band light RN according to detection signals from light amount detectors 38a, 40a and 41a attached to the white light optical fiber 38, the blue narrow band light optical fiber 40 and the red narrow band light optical fiber 41. The monitoring unit 34 monitors the degree of differences of the light amounts of the white light W, blue narrow band light BN and red narrow band light RN being monitored from a light amount of a predetermined standard condition. The amount of the difference of the detected light amounts is transmitted to the light amount controller 35.

The light amount controller 35 controls driving of the excitation light source 30a, the blue narrow band light source 31 and the red narrow band light source 32 according to the amount of the difference between the light amounts in the standard condition detected by the monitoring unit 34. This control adjusts the light amounts of the white light W, blue narrow band light BN and red narrow band light RN at the light amounts of the standard condition.

The electronic endoscope 11 includes the light guide 43, a CCD 44 (image signal acquisition device), an analog processing circuit 45 (AFE: analog front end), and an imaging controller 46. The light guide 43 is an optical fiber, bundle fiber or the like of a large diameter. An entrance end of the light guide 43 is entered in a coupler 36 inside the illuminator. An exit end of the light guide 43 is directed to a lighting lens 48 disposed in the tip device 16a. Light conducted by the light guide 43 is irradiated to the inside of the subject body through the lighting lens 48 and a lighting window 49, which is disposed at an end surface of the tip device 16a. The reflected light reflected inside the subject body passes through a viewing window 50 disposed at the end surface of the tip device 16a, and enters a condensing lens 51. The CCD 44 is a color CCD, in which B pixels with color filters of the B color, G pixels with color filters of the G color, and R pixels with color filters of the R color are arranged on an imaging surface 44a.

The AFE 45 is constituted by a correlated double sampling circuit (CDS), an automatic gain control circuit (AGC), and an analog/digital converter (A/D) (all not shown). The CDS processes an image signal from the CCD 44 in the correlated double sampling and eliminates noise created by driving of the CCD 44. The AGC amplifies the image signal after eliminating the noise in the CDS. The A/D converts the image signal amplified by the AGC into a digital image signal of a predetermined bit number, and inputs this to the processing apparatus 12.

The imaging controller 46 is connected to the controller 59 in the processing apparatus 12, and sends a drive signal to the CCD 44 in response to command from the controller 59. The CCD 44 outputs an image signal to the AFE 45 at a predetermined frame rate according to the drive signal from the imaging controller 46.

The processing apparatus 12 includes a normal light image generator 55, a frame memory 56, a special light image generator 57 (image generator with a receiver) and a display control circuit 58, the normal light image generator 55 generating a normal light image, the special light image generator 57 generating an oxygen saturation level image by visualizing an oxygen saturation level of superficial blood vessels or intermediate and deep blood vessels, the controller 59 controlling the various elements.

Figure 3A:
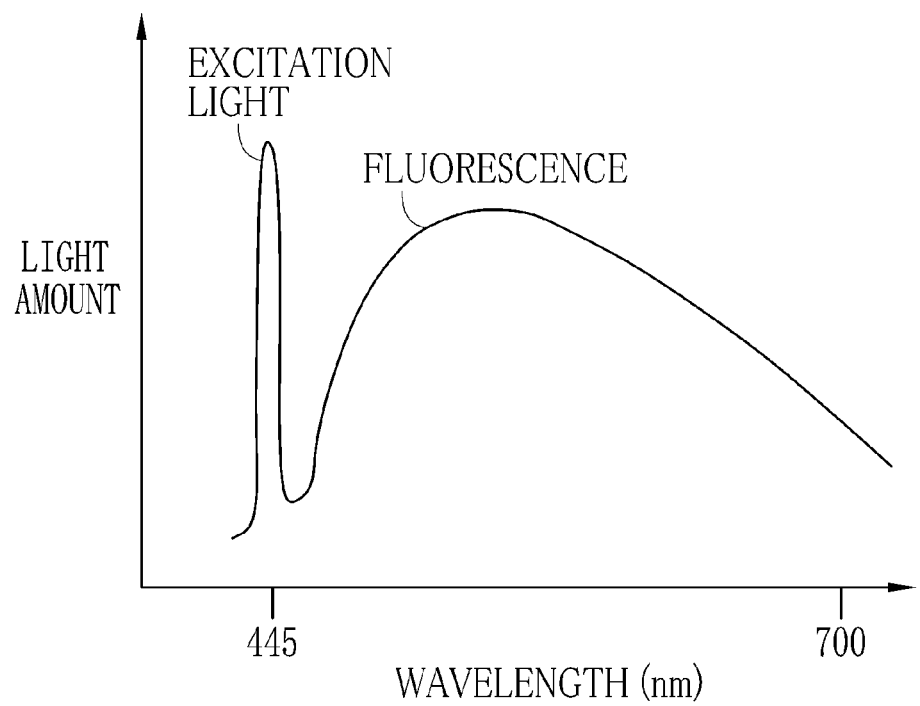
FIG. 3A is a graph illustrating an emission spectrum of white light W of excitation emission with excitation light.

As illustrated in FIG. 3A, the white light W is light of mixed color in combination of excitation light with a center wavelength of 445 nm and a wavelength range of 440-460 nm, and fluorescence with a wavelength range from bluish green to red, for example, as wide as 460-700 nm. The white light W is in a wide wavelength range from blue to red. Accordingly, the white light W is used for generating a normal light image in which a visible light image of the subject body is formed.

Figure 3B:
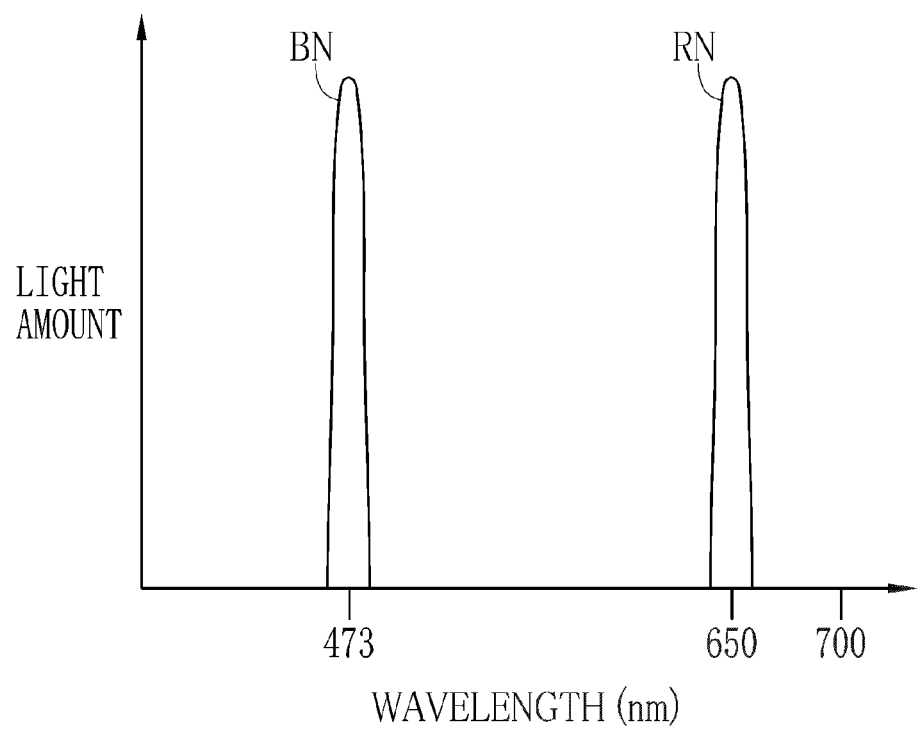
FIG. 3B is a graph illustrating emission spectra of blue narrow band light EN and red narrow band light RN.

As illustrated in FIG. 3B, the blue narrow band light BN has a center wavelength of 473 nm and is limited in the wavelength range of 460-480 nm. The blue narrow band light BN is light of the wavelength range with a depth of penetration to the superficial blood vessels, and in the wavelength range with different absorption coefficients between the oxyhemoglobin HbO2 and deoxyhemoglobin Hb as illustrated in FIG. 4. Thus, the blue narrow band light BN is used for measuring an oxygen saturation level of the superficial blood vessels. Note that the light of the wavelength range of 470-700 nm has the property of a small scattering coefficient in mucosal tissue and a small dependency to the wavelength. Thus, the use of the light of this wavelength range for lighting can decrease influence of the depth of blood vessels and can obtain blood information inclusive of information of a blood amount and oxygen saturation level.

As illustrated in FIG. 3B, the red narrow band light RN has a center wavelength of 650 nm and is limited in the wavelength range of 640-660 nm. The red narrow band light RN is light of the wavelength range with a depth of penetration to the intermediate and deep blood vessels, and in the wavelength range with different absorption coefficients between the oxyhemoglobin HbO2 and deoxyhemoglobin Hb as illustrated in FIG. 4. Thus, the red narrow band light RN is used for measuring an oxygen saturation level of the intermediate and deep blood vessels.

As illustrated in FIG. 5, a color filter of the B color at the B pixels of the CCD 44 has a spectral transmittance indicated by a curve 52, and transmits the white light W and blue narrow band light BN. A color filter of the G color at the G pixels has a spectral transmittance indicated by a curve 53, and transmits the white light W and blue narrow band light BN. A color filter of the R color at the R pixels has a spectral transmittance indicated by a curve 54, and transmits the white light W and red narrow band light RN.

Figure 6A:
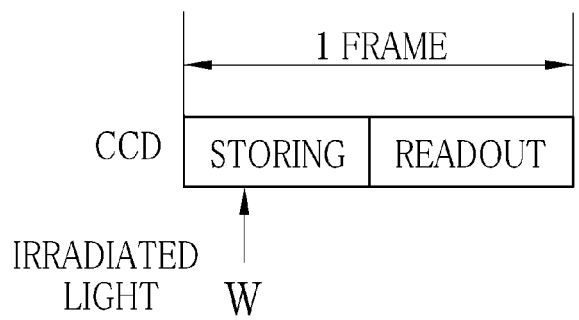
FIG. 6A is an explanatory view illustrating an imaging control of the CCD in the normal imaging mode in the first embodiment.

The imaging controller 46 performs control of imaging differently between the modes. While the normal imaging mode is set, a step of storing a signal charge by photoelectric conversion of image light of the white light W and a step of readout of the stored signal charge are carried out within a frame period of one frame as illustrated in FIG. 6A. The imaging control for the one frame is performed repeatedly while the normal imaging mode is set. Note that a blue signal Bc output by the B pixel of the CCD 44, a green signal Gc output by the G pixel, and a red signal Rc output by the R pixel are obtained at each of the readout steps of a signal charge in the normal imaging mode.

Figure 6B:
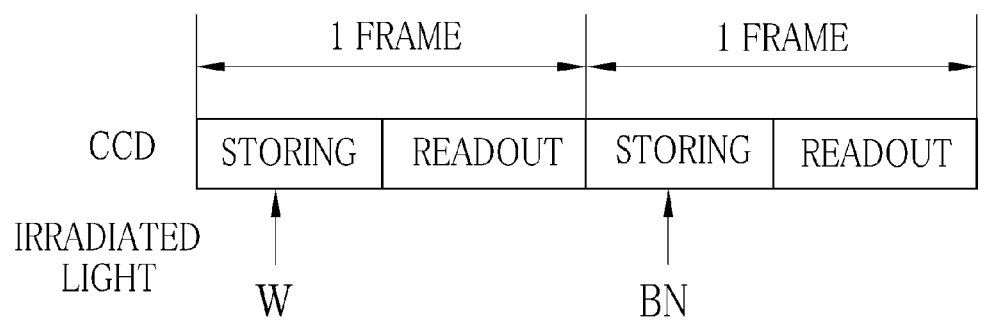
FIG. 6B is an explanatory view illustrating an imaging control of the CCD in the surface imaging mode in the first embodiment.

While the surface imaging mode is set, a step of storing a signal charge by photoelectric conversion of image light of the white light W and a step of readout of the stored signal charge are carried out within a frame period of one frame as illustrated in FIG. 6B. After this, a step of storing a signal charge by photoelectric conversion of image light of the blue narrow band light BN and a step of readout of the stored signal charge are carried out within a frame period of one frame. The imaging control for the two frames is performed repeatedly while the surface imaging mode is set.

In the surface imaging mode, a blue signal Bs1 output from the B pixel in the CCD 44, a green signal Gs1 output from the G pixel, and a red signal Rs1 output from the R pixel are obtained initially at a first frame. Then a blue signal Bs2 output from the B pixel, a green signal Gs2 output from the G pixel, and a red signal Rs2 output from the R pixel are obtained next at a second frame. The signal Bs2 of the second frame includes information related to the oxygen saturation level of the superficial blood vessels, because obtained by imaging the image light of the blue narrow band light BN. The signal Gs1 of the first frame is used for normalizing the signal Bs2 of the second frame as a reference signal.

Figure 6C:
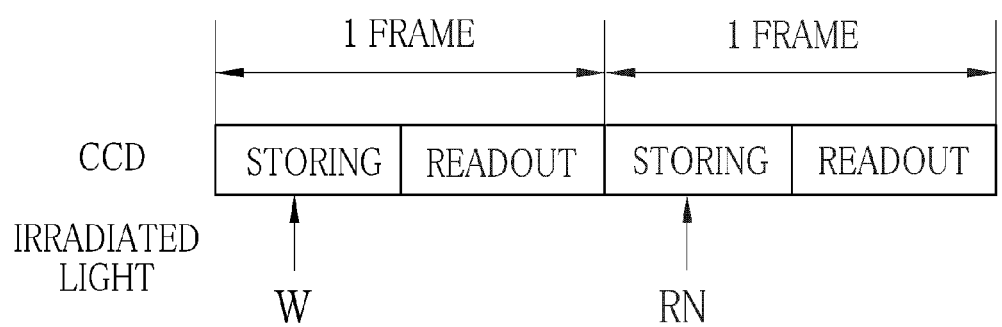
FIG. 6C is an explanatory view illustrating an imaging control of the CCD in the intermediate and deep imaging mode in the first embodiment.

While the intermediate and deep imaging mode is set, a step of storing a signal charge by photoelectric conversion of image light of the white light W and a step of readout of the stored signal charge are carried out within a frame period of one frame as illustrated in FIG. 6C. After this, a step of storing a signal charge by photoelectric conversion of image light of the red narrow band light RN and a step of readout of the stored signal charge are carried out within a frame period of one frame. The imaging control for the two frames is performed repeatedly while the intermediate and deep imaging mode is set.

In the intermediate and deep imaging mode, a blue signal Bd1 output from a B pixel in the CCD 44, a green signal Gd1 output from a G pixel, and a red signal Rd1 output from an R pixel are obtained initially at a first frame. Then a blue signal Bd2 output from the B pixel, a green signal Gd2 output from the G pixel, and a red signal Rd2 output from the R pixel are obtained next at a second frame. The signal Rd2 of the second frame includes information related to the oxygen saturation level of the intermediate and deep blood vessels, because obtained by imaging the image light of the red narrow band light RN. The signal Gd2 of the first frame includes information of reference light after wavelength separation of white light with a color filter of the G pixel on the CCD 44. The signal Gs2 is used for normalizing the signal Rd2 of the second frame as a reference signal.

Figure 7:
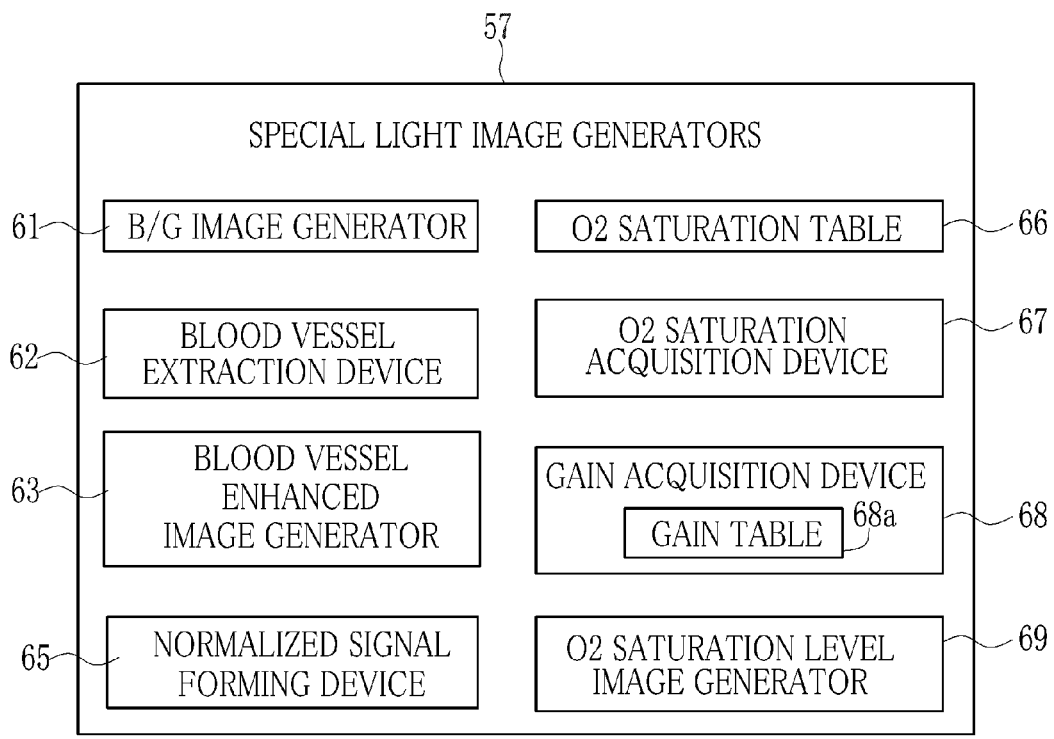
FIG. 7 is a block diagram illustrating a special light image generator.

As illustrated in FIG. 7, the special light image generator 57 generates a blood vessel enhanced image in which superficial blood vessels or intermediate and deep blood vessels are enhanced in a normal light image by use of a B/G image generating device 61, a blood vessel extraction device 62 and a blood vessel enhanced image generating device 63.

Also, the special light image generator 57 generates an oxygen saturation image in which information of the oxygen saturation level is considered in the blood vessel enhanced image by use of a normalized signal forming device 65, an oxygen saturation table 66, an oxygen saturation acquisition device 67, a gain acquisition device 68 and an oxygen saturation level image generating device 69.

The B/G image generating device 61 generates a B/G image according to the blue and green signals B and G included in the signals obtained by imaging of image light of the white light. Pixels of the B/G image include information of a luminance ratio B/G after dividing the signal value of the blue signal B by the signal value of the green signal G. In the case of the surface imaging mode, a B/G image is generated according to Bs1 and Gs1. In the case of the intermediate and deep imaging mode, a B/G image is generated according to Bd1 and Gd1.

Figure 8:
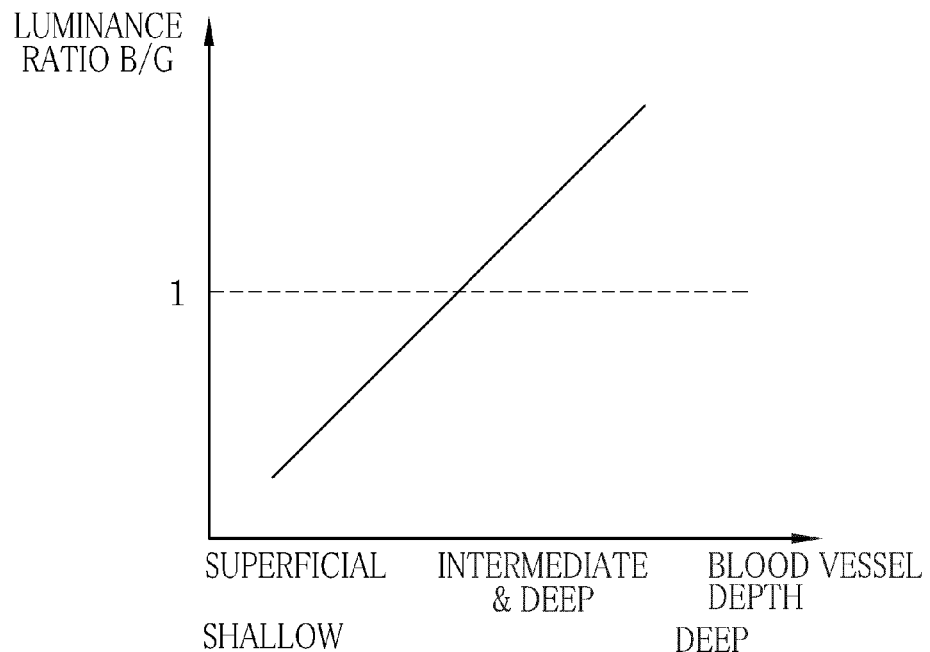
FIG. 8 is a graph illustrating a relationship between a luminance ratio B/G and a depth of a blood vessel.
Figure 9:
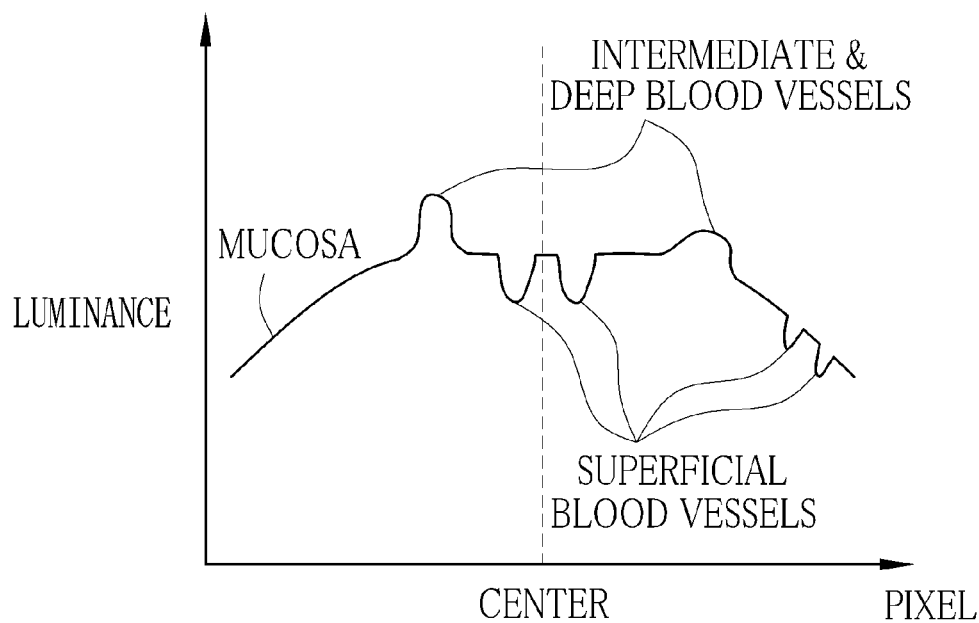
FIG. 9 is a graph illustrating luminance distribution of a part of a B/G image.

The luminance ratio B/G of the respective pixels in the B/G image has relevancy to a depth of blood vessels. As illustrated in FIG. 8, the luminance ratio B/G increases according to an increase in the depth of blood vessels. Thus, a relationship of the largeness and smallness of "luminance of the superficial blood vessels<luminance of the mucosa<luminance of the intermediate and deep blood vessels" is satisfied. Note that luminance of the B/G image can be in a distribution with a highest level at the central portion and a lower level according to nearness to the periphery from the center due to such factors as unevenness in illumination, as depicted in the B/G image of FIG. 9. Therefore, the above-described relationship (luminance of the superficial blood vessels<luminance of the mucosa<luminance of the intermediate and deep blood vessels) is satisfied locally but not satisfied macroscopically.

Figure 10:
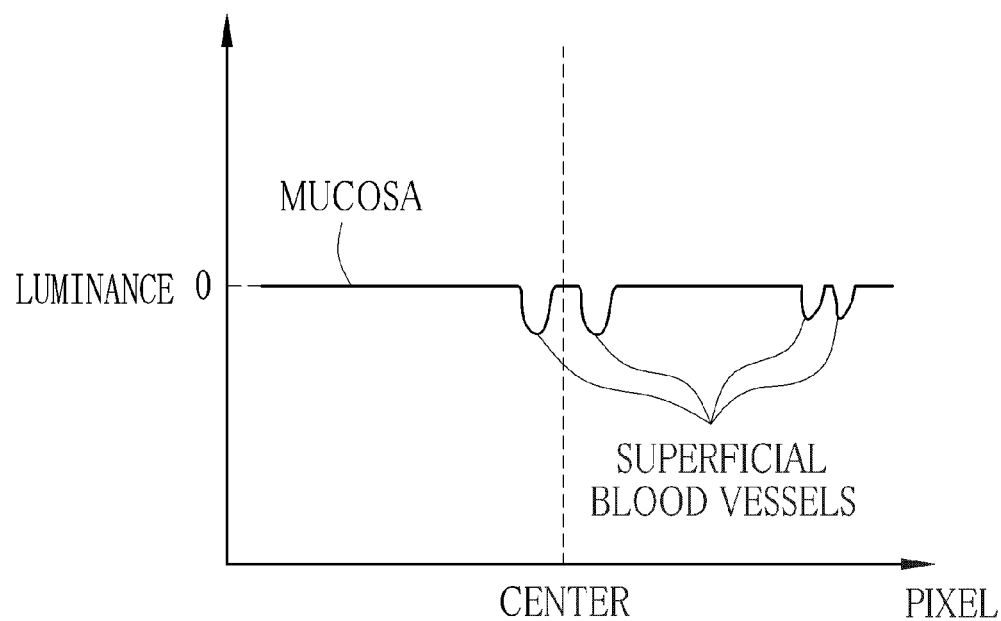
FIG. 10 is a graph illustrating luminance distribution of a part of a superficial blood vessel extraction image.

The blood vessel extraction device 62 extracts blood vessels disposed in particular depth according to the B/G image. The blood vessel extraction is carried out by processing of frequency filtering. While the surface imaging mode is set, a high frequency component is extracted from the B/G image as a frequency band component remarkable in the superficial blood vessels. As illustrated in FIG. 10, a superficial blood vessel extraction image is obtained with a negative luminance of the superficial blood vessels and "0" luminance of mucosal tissue. Only the superficial blood vessels are extracted sharply in the superficial blood vessel extraction image.

Figure 11:
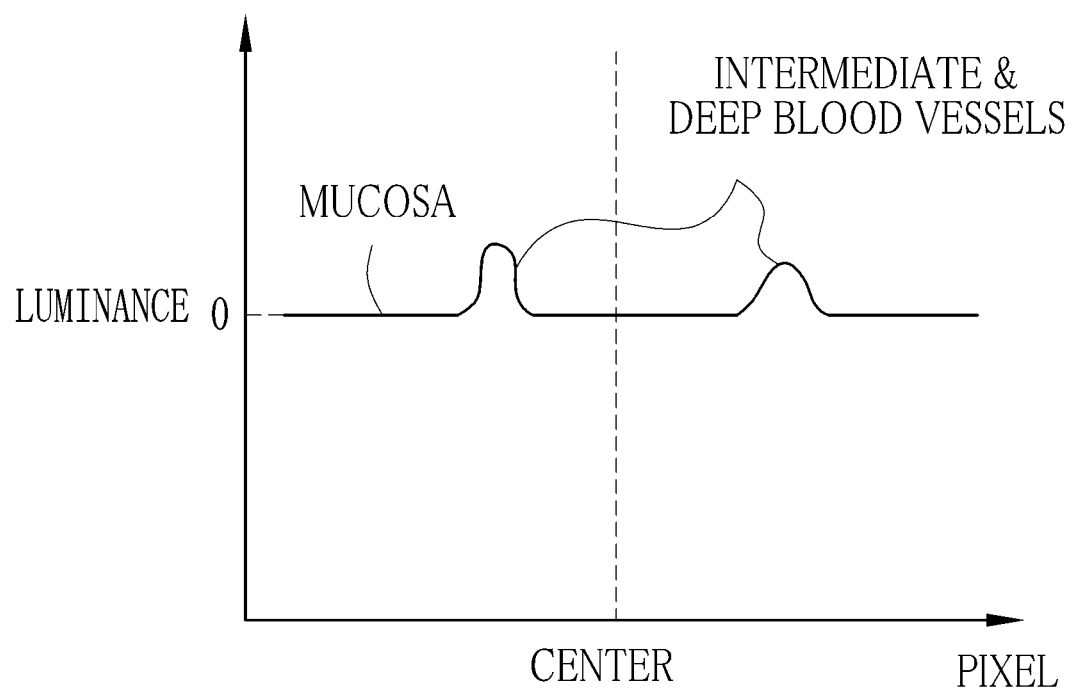
FIG. 11 is a graph illustrating luminance distribution of a part of an intermediate and deep blood vessel extraction image.

On the other hand, while the intermediate and deep imaging mode is set, a medium frequency component which is a remarkable frequency component in the intermediate and deep blood vessels is extracted from the B/G image. Thus, an intermediate and deep blood vessel extraction image is obtained as illustrated in FIG. 11 in which luminance of the intermediate and deep blood vessels is positive and luminance of the mucosal tissue is substantially "0". In the intermediate and deep blood vessel extraction image, only the intermediate and deep blood vessels are sharply extracted.

As the frequency filtering is carried out as described above, a component of the mucosa becomes as small a luminance as "0". Only the part of the blood vessels can be extracted. Also, the above-described relationship of the largeness and smallness (luminance of the superficial blood vessels<luminance of the mucosa<luminance of the intermediate and deep blood vessels) can be satisfied macroscopically.

The blood vessel enhanced image generating device 63 creates the superficial blood vessel enhanced image in enhancement of superficial blood vessels from the superficial blood vessel extraction image and the normal light image, and creates the intermediate and deep blood vessel enhanced image from the intermediate and deep blood vessel extraction image and the normal light image. While the surface imaging mode is set, synthesis between the superficial blood vessel extraction image and the normal light image is carried out to create the superficial blood vessel enhanced image. While the intermediate and deep imaging mode is set, synthesis between the intermediate and deep blood vessel extraction image and the normal light image is carried out to create the intermediate and deep blood vessel enhanced image. Note that it is preferable to convert the pixel value to an absolute value in a "positive" form, because the pixel value of the vascular portions in the superficial blood vessel extraction image is "negative".

The normalized signal forming device 65 generates a normalized signal by dividing the oxygen saturation level signal by the reference signal, the oxygen saturation level signal including information related to the oxygen saturation level. In case the surface imaging mode is set, the normalized signal forming device 65 divides Bs2 as the oxygen saturation level signal by Gs1 as the reference signal to obtain the normalized signal Bs2/Gs1 for the superficial blood vessels. On the other hand, in case the intermediate and deep imaging mode is set, Bd2 as the oxygen saturation level signal is divided by Gd1 as the reference signal to obtain the normalized signal Bd2/Gd1 for the intermediate and deep blood vessels.

Figure 12:
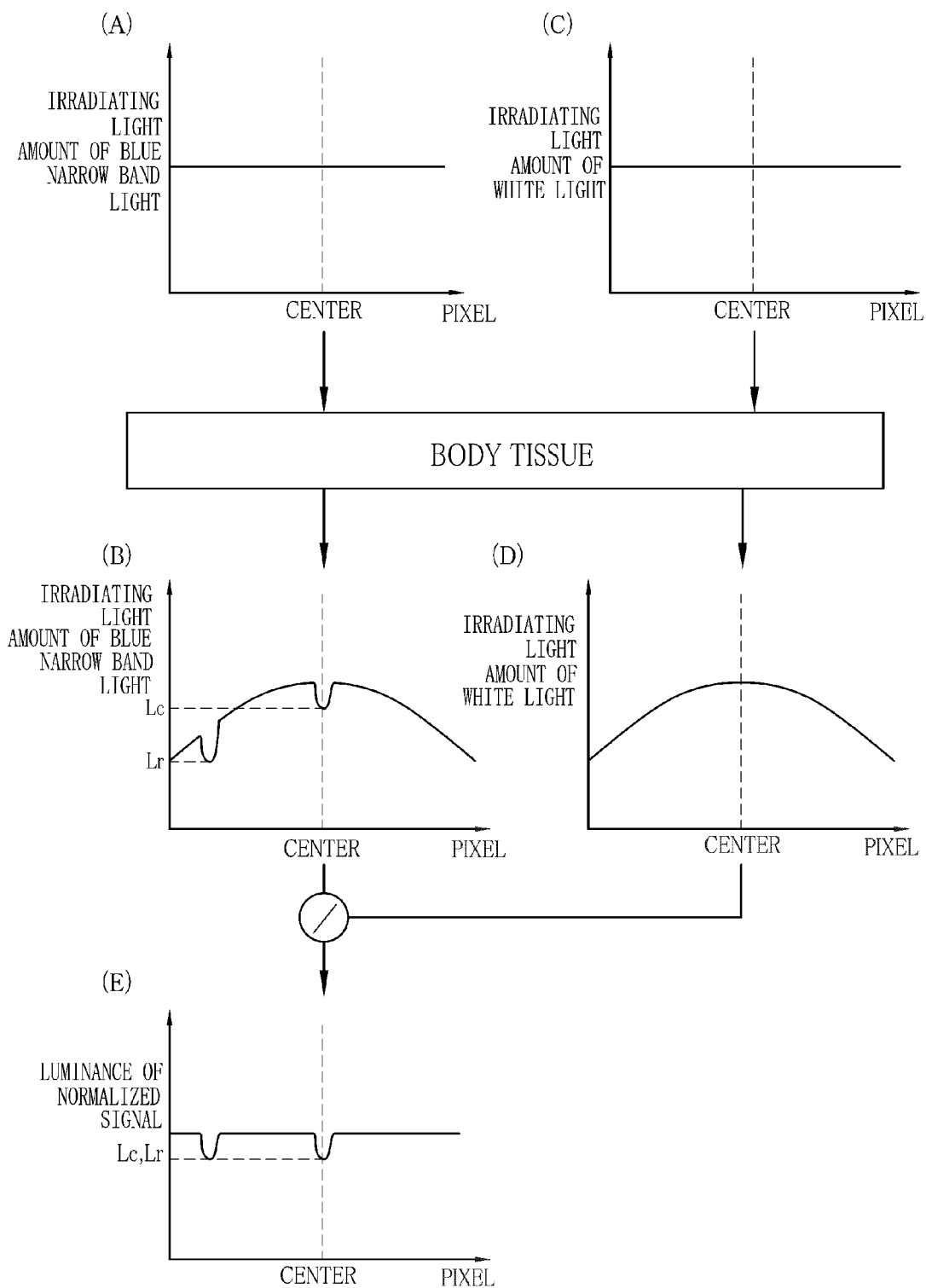
FIG. 12 is a view illustrating a method of forming a normalized signal.

Reasons for the normalization in the normalized signal forming device 65 are hereinafter described with an example of the surface imaging mode. For example, in case the blue narrow band light BN with an entirely uniform distribution of the light amount is irradiated to body tissue with uneven shapes as illustrated in FIG. 12(A), a distribution of a light amount of this reflected light is a non-uniform distribution as illustrated in FIG. 12(B). Even in case portions with a substantially equal characteristic of light absorption are present in central and peripheral regions of the body tissue, there occurs a difference between a luminance value Lc of the portion in the central region and a luminance value Lr of the portion in the peripheral region. In short, it is likely that the signal Bs2 obtained by imaging of a reflection image of the blue narrow band light BN comes to include information with low reliability for the oxygen saturation level with a difference in the luminance value despite the equality in the oxygen condition.

Thus, as illustrated in FIG. 12(C), white light with a uniform distribution of a light amount is irradiated separately from the blue narrow band light BN. Then, as illustrated in FIG. 12(D), a reflection image of the white light of a non-uniform distribution of the light amount owing to the uneven shape of the body tissue is created by imaging. A signal Gs1 obtained by this imaging includes uneven shape information of the body tissue. As illustrated in FIG. 12(E), the signal Bs2 is normalized by dividing the signal Bs2 by the signal Gs1.

Consequently, the uneven shape information can be deleted from the signal Bs2 as the luminance value becomes uniform in the portions without the information of the oxygen saturation level. Also, the portions of which the characteristic of the light absorption is equal are expressed with an equal luminance value (luminance value Lc of the central region=luminance value Lr of the peripheral region). Thus, the normalized signal Bs2/Gs1 can include the information of the oxygen saturation level with high reliability.

It is preferable for the light used as reference light to have a wavelength different from the light for the oxygen saturation level, such as the blue narrow band light BN. For example, the light can be narrow band light with a color other than the green and with a wavelength different from the blue narrow band light BN, and also can be broad band light such as white light. Also, the signal for normalization is Gs1, but can be Bs1 or Rs1 instead. Also, the signal for normalization can be Gs2 or Rs2 acquired at the second frame in the same manner as Bs2.

The oxygen saturation table 66 stores a relationship between the normalized signal and the oxygen saturation level as obtained according to past diagnoses, experiences and the like. As illustrated in FIG. 13 with the oxygen saturation table 66, assuming that a signal value of the normalized signal is, for example, in a range of a1-a2, then the oxygen saturation level corresponding to this range is S1 (%). The oxygen saturation acquisition device 67 acquires the oxygen saturation level corresponding to the normalized signal formed by the normalized signal forming device 65 according to the oxygen saturation table 66.

Note that a signal value of the signal Bs2 is changed with a change in the oxygen saturation level. It is possible to view the oxygen saturation level to a certain extent by a change in the brightness of the blood vessel even without normalization with a reference signal such as a signal Gs1. However, the brightness of the blood vessels may change upon a change of overall brightness in the body cavity in the operation of the AE for imaging of the oxygen saturation level with a change in the brightness of the blood vessels. Accordingly, the oxygen saturation level is acquired as objective numerical information according to the present invention, without receiving the oxygen saturation level as brightness of the blood vessels. To this end, a relationship of associating the signal ratio Bs2/Gs1 with the oxygen saturation level is used.

Reasons for associating the signal ratio Bs2/Gs1 with the oxygen saturation level without using the signal Bs1 are hereinafter described. The signal value of the signal Bs2 is changed not only by a change in the oxygen saturation level but also by a change in an imaging distance. For example, the signal value of the signal Bs2 is relatively high in the low oxygen condition. However, the signal value of the signal Bs2 decreases in the far distance condition by positioning the tip device 16a of the electronic endoscope distantly from the body tissue. In this situation, the signal value of the signal Bs2 does not correctly express the oxygen saturation level.

Thus, the signal Gs1 is obtained besides the signal Bs2 as a signal for referring to a change in the brightness in the body cavity according to change in the imaging distance. In case the inside of the body cavity becomes dim, both of the signal values of the signals Bs2 and Gs1 are decreased. However, in case the inside of the body cavity becomes bright, both of their signal values are increased. Accordingly, a signal value of the normalized signal Bs2/Gs1 after dividing the signal Bs2 by the signal Gs1 does not change even though the brightness in the body cavity is changed. In short, the signal value of the normalized signal Bs2/Gs1 expresses the oxygen saturation level correctly, and can be associated with the oxygen saturation level.

Also, in the first embodiment, the white light W, blue narrow band light BN and red narrow band light RN for use in determining the oxygen saturation level is adjusted at light amounts of the standard condition in the illuminator 13. The signals Bs2, Gs1, Rd2 and Gd1 obtained by imaging the image light of the light components in the color CCD 44 are adjusted at signal values of the standard condition on the assumption of no presence of a lesion or other abnormal part. Therefore, the oxygen saturation level of blood vessels of a particular depth can be determined with good precision, owing to the adjustment at the signal values of the standard condition and generation of normalized signals Bs2/Gs1 and Rd2/Gd1 according to the signal values.

The gain acquisition device 68 determines a gain for adjusting a pixel value of the blood vessel enhanced image according to the oxygen saturation level obtained by the oxygen saturation acquisition device 67. A gain table 68*a* is provided in the gain acquisition device 68, in which a relationship between the oxygen saturation level and the gain is stored. Examples of the gain include a gain gr for adjusting a pixel value of a red signal R of the blood vessel enhanced image, a gain gg for adjusting a pixel value of a green signal G, and a gain gb for adjusting a pixel value of a blue signal B. The gain acquisition device 68 determines the gains gb, gg and gr according to the oxygen saturation level obtained by the oxygen saturation acquisition device 67 by use of the gain table 68*a*.

Figure 14A:
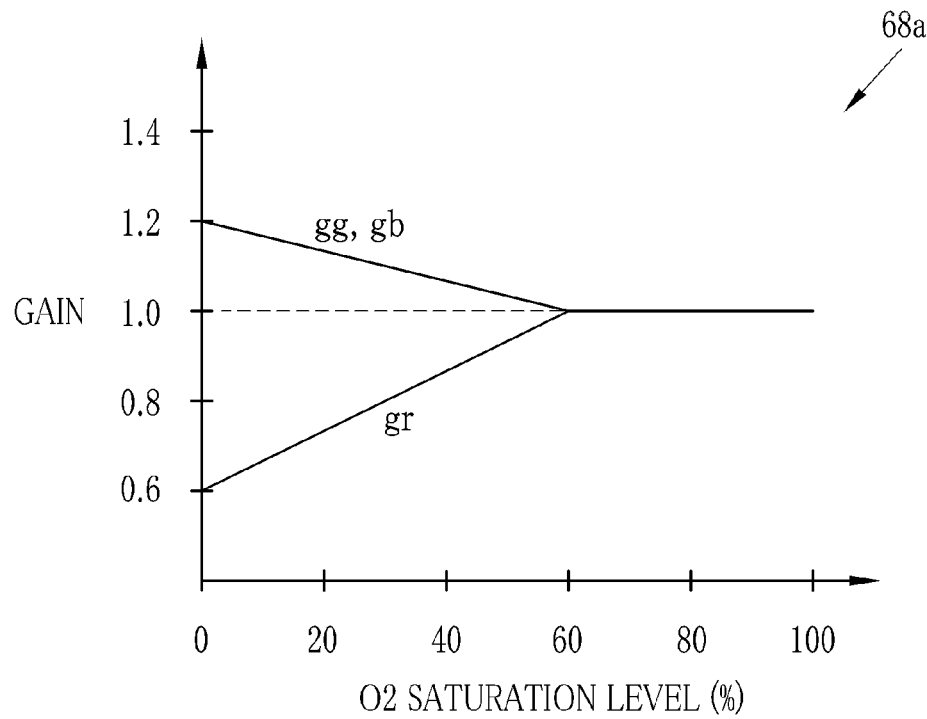
FIG. 14A is a graph illustrating a gain table in which the oxygen saturation level is associated with a gain.

Note that in the gain table 68*a*, all the gains gb, gg and gr are set at 1 while the oxygen saturation level is 100-60% as illustrated in FIG. 14A. On the other hand, the gain gr is set to decrease gradually according to a decrease in the oxygen saturation level in case the oxygen saturation level becomes lower than 60%, and the gains gg and gb are set to increase gradually according to the decrease in the oxygen saturation level.

The oxygen saturation level image generating device 69 multiplies the gains gb, gg and gr from the gain acquisition device 68 by the pixel values of the signals B, G and R of the blood vessel enhanced image, to generate the oxygen saturation level image having the signals B', G' and R' ((B', G', R')=(gb×B, gg×G, gr×R)). Note that the oxygen saturation level is adjusted by adjusting a pixel value of the blood vessel enhanced image according to the oxygen saturation level in the present embodiment. However, it is possible to adjust a color characteristic of the blood vessel enhanced image according to the oxygen saturation level, such as a hue, luminance or chroma. For this structure, a hue matrix, luminance matrix or chroma matrix is used in place of the gain table 68*a* described above, for associating the pixel value of the blood vessel enhanced image with a conversion value for conversion into the hue, luminance or chroma. Furthermore, the oxygen saturation level image can be generated according to a chrominance signal associated with the oxygen saturation level and a luminance signal of assignment of a signal (for example, Gs1) expressing an average brightness in the body cavity, instead of generating the oxygen saturation level image by considering the oxygen saturation level with the blood vessel enhanced image (for example, the chrominance signal Cr can be set larger than the chrominance signal Cb at the time of a high oxygen condition, and the chrominance signal Cb can be set larger than the chrominance signal Cr at the time of a low oxygen condition).

Figure 14B:
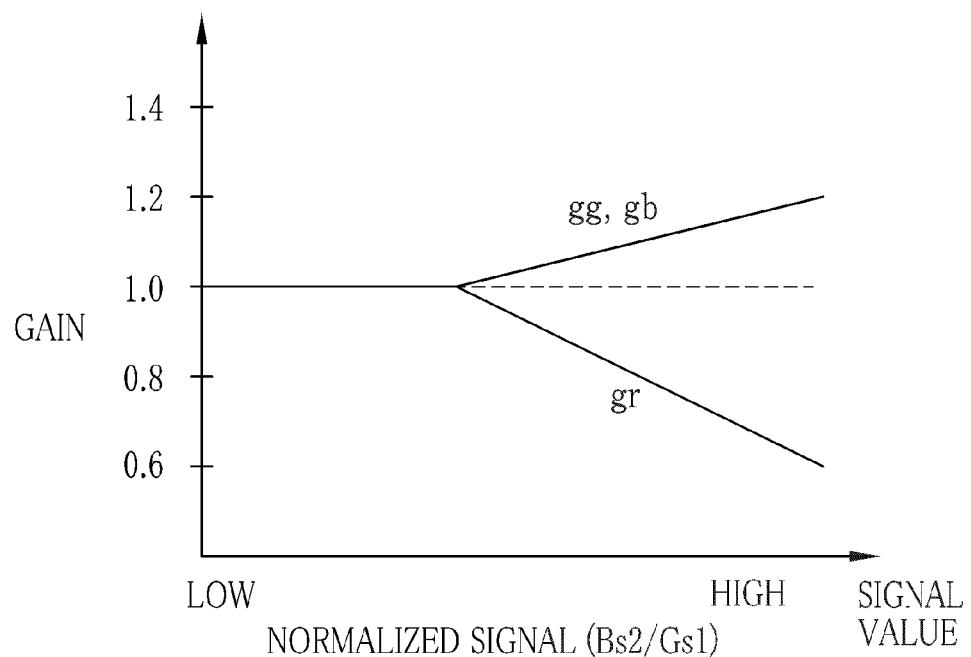
FIG. 14B is a graph illustrating a gain table in which the normalized signal is associated with a gain.

Although the oxygen saturation level is associated with the gains in the gain table 68*a*, it is possible instead to associate the normalized signal Bs2/Gs1 with the gains as illustrated in FIG. 14B. Assuming that the signal value of the normalized signal Bs2/Gs1 is small, the oxygen saturation level is high in FIG. 14B. The gains gb, gg and gr are set at "1". The oxygen saturation level becomes lower according to highness of the signal value. In compliance with this, the gains gb and gg are set higher than "1" and gr is set lower than "1" in contrast.

Figure 15:
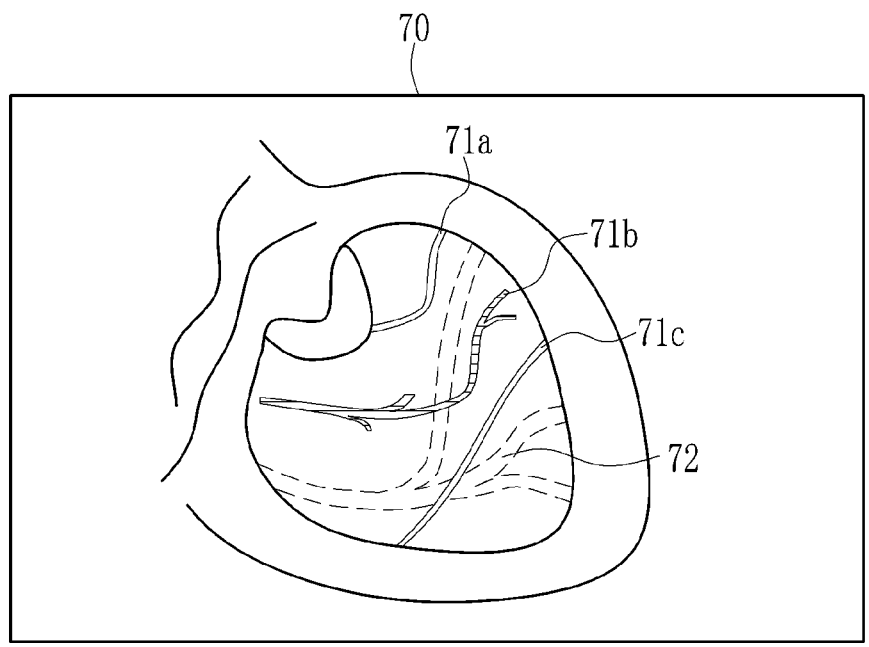
FIG. 15 is a image view illustrating an oxygen saturation level image in which information of the oxygen saturation level is considered in a superficial blood vessel enhanced image.

The display control circuit 58 displays an oxygen saturation level image on the monitor 14. While the surface imaging mode is set, an oxygen saturation level image 70 illustrated in FIG. 15 is displayed on the monitor 14. Among plural superficial blood vessels 71*a*, 71*b* and 71*c* enhanced in the oxygen saturation level image 70, the superficial blood vessels 71*b* are locally expressed in the pseudo color owing to the low oxygen condition with the oxygen saturation level lower than 60%. On the other hand, the remaining superficial blood vessels 71*a* and 71*c* are expressed in the color normally suitable for blood vessels owing to the oxygen saturation level higher than 60%.

This is because the pixel value changes with the superficial blood vessels 71*b* of which the gains gb, gg and gr are different from "1" and because the pixel value does not change with the superficial blood vessels 71*a* and 71*c* of which the gains gb, gg and gr are "1". The oxygen saturation level image is based on the superficial blood vessel enhanced image, which is further based on the normal light image. Thus, the superficial blood vessels 71*a* and 71*c*, intermediate and deep blood vessels 72, mucosa and the like are in the color balance normally suitable to the body tissue, except for the superficial blood vessels 71*b* expressed in the pseudo color in the lower oxygen condition. Accordingly, performance for diagnosis can be totally higher, as objects of interest such as blood vessels appear reliably to express information in the pseudo color or the like, and remaining parts appear as a normal view image.

Figure 16:
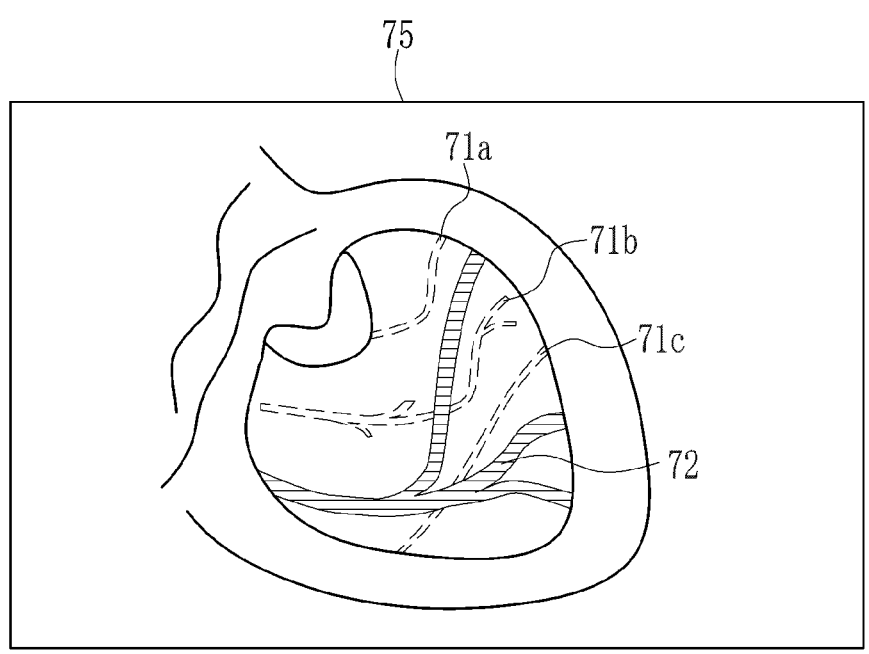
FIG. 16 is a image view illustrating an oxygen saturation level image in which information of the oxygen saturation level is considered in an intermediate and deep blood vessel enhanced image.

While the intermediate and deep imaging mode is set, an oxygen saturation level image 75 as illustrated in FIG. 16 is displayed on the monitor 14. The intermediate and deep blood vessels 72 enhanced in the oxygen saturation level image 75 are expressed in the pseudo color because of the low oxygen condition with the oxygen saturation level lower than 60%. On the other hand, remaining blood vessels and mucosa are in the colors suitable for the normal body tissue.

It is possible to visualize the oxygen saturation level in all the regions inclusive of the superficial and intermediate and deep tissue in the body tissue by combined use of the oxygen saturation level image 70 for the surface and the oxygen saturation level image 75 for the intermediate and deep tissue at the time of diagnosis as described above. Also, the oxygen saturation level image 70 of the surface is generated according to the signals Bs2 and Gs1 of the two wavelengths. The oxygen saturation level image 75 of the intermediate and deep tissue is generated according to the signals Rd2 and Gd1 of the two wavelengths. It is unnecessary to use signals of three wavelengths for visualizing the oxygen saturation level as used conventionally. Furthermore, the signals of the two wavelengths are acquired in two frames. Thus, the frame rate can be kept from decreasing in comparison with the conventional technique in which the signals of the three wavelengths are acquired in three frames.

Figure 17:
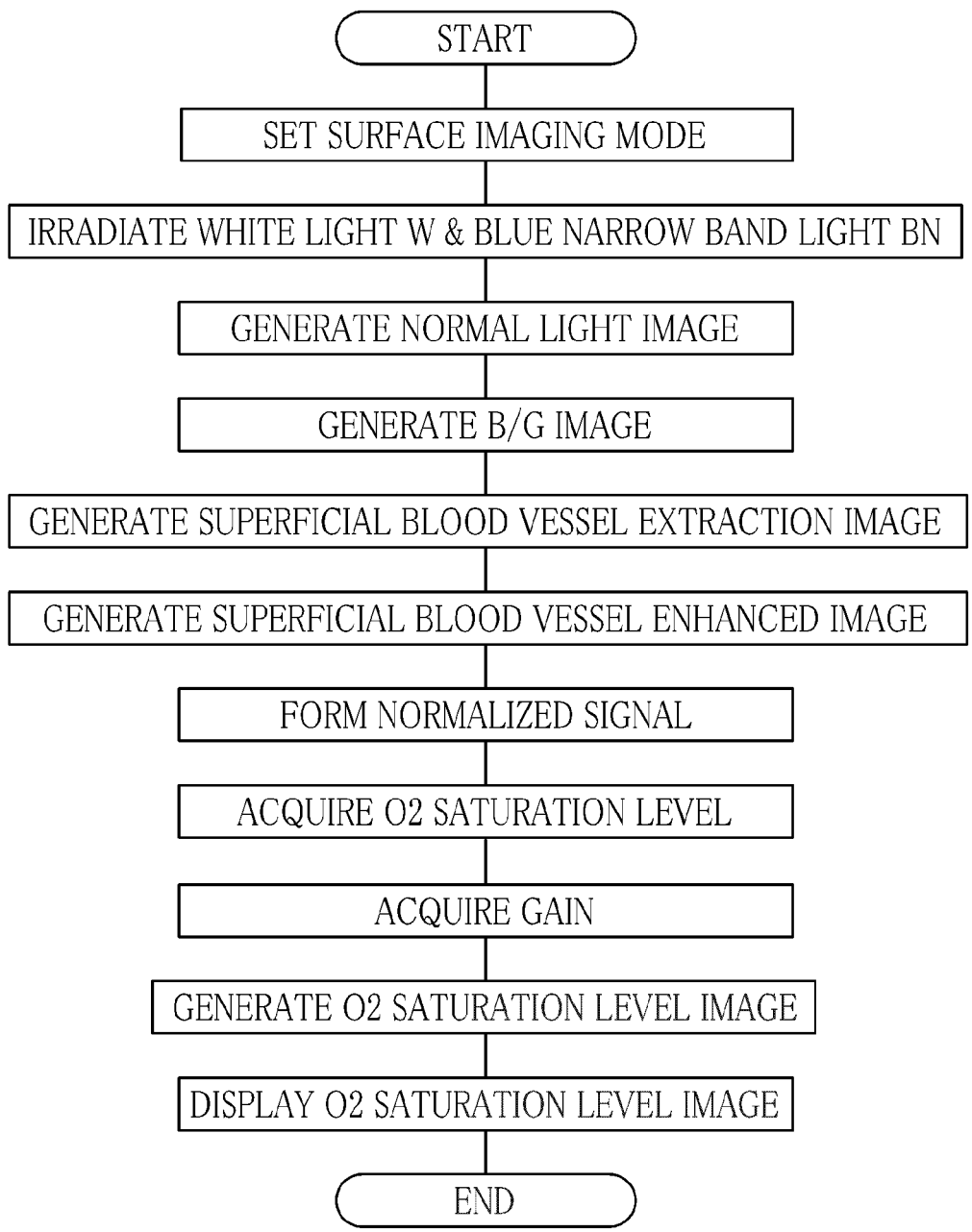
FIG. 17 is a flow chart illustrating step of the surface imaging mode.

A sequential flow in the surface imaging mode is described next by use of a flow chart illustrated in FIG. 17. (A sequential flow in the intermediate and deep imaging mode is omitted in the description because substantially the same as the surface imaging mode.) Note that the elongated tube 16 is entered in a subject body, for example, a gastrointestinal tract in the normal imaging mode. The tip device 16*a* is set at a desired imaging area by manipulating the angle adjusting wheels 21, to perform normal imaging. In the normal imaging, a normal light image of the color of the imaging area illuminated with the white light W is displayed on the monitor 14.

In case the imaging area is found to be a lesion in the normal imaging mode, the mode changeover SW 15 changes over to the surface imaging mode. Thus, the white light W and blue narrow band light BN is irradiated to the subject body alternately. The subject body illuminated with the white light W is imaged by the color CCD 44, which outputs a blue signal Bs1, a green signal Gs1 and a red signal Rs1. Also, the subject body illuminated with the blue narrow band light BN is imaged by the CCD 44, which outputs a blue signal Bs2, a green signal Gs2 and a red signal Rs2.

A normal light image is generated next according to the blue color signal Bs2, green color signal Gs2 and red color signal Rs2. Also, the B/G image according to a luminance ratio B/G between the blue color signal Bs2 and the green color signal Gs2 is generated. A superficial blood vessel is extracted from the B/G image upon generating the B/G image. Thus, a superficial blood vessel extraction image is obtained. As the blood vessel is extracted from the B/G image, a superficial blood vessel enhanced image is generated by synthesizing the normal light image with the superficial blood vessel of which the luminance value is converted into an absolute value.

Then the blue signal Bs2 is divided by the green signal Gs1 to create the normalized signal Bs2/Gs1. An oxygen saturation level according to the normalized signal Bs2/Gs1 is obtained from the oxygen saturation table 66. Then gains gb, gg and gr according to the obtained oxygen saturation level is acquired from the gain table 68a. The acquired gains gb, gg and gr are multiplied by the pixel values of the color signals of the superficial blood vessel enhanced image, to generate the oxygen saturation level image 70 for the surface. The oxygen saturation level image 70 of the surface being generated is displayed by the monitor 14.

In the second embodiment of the present invention, illumination is carried out by a method of a rotational filter. In an endoscope system 100 of the second embodiment, an illuminator 105 is used as illustrated in FIG. 18, including a broad band light source 101, a rotary filter 102 and a motor 103. The broad band light source 101 emits broad band light BB with a wavelength range of 400-700 nm. The rotary filter 102 sequentially causes passage of light of plural types with different wavelengths by wavelength separation of the broad band light BB from the broad band light source 101. The motor 103 rotates the rotary filter 102 at a constant speed. Note that imaging control for the CCD 44 is different from the first embodiment because a subject body is imaged according to the method of the rotational filter. However, remaining elements are the same as the first embodiment. Their description is omitted.

Figure 19:
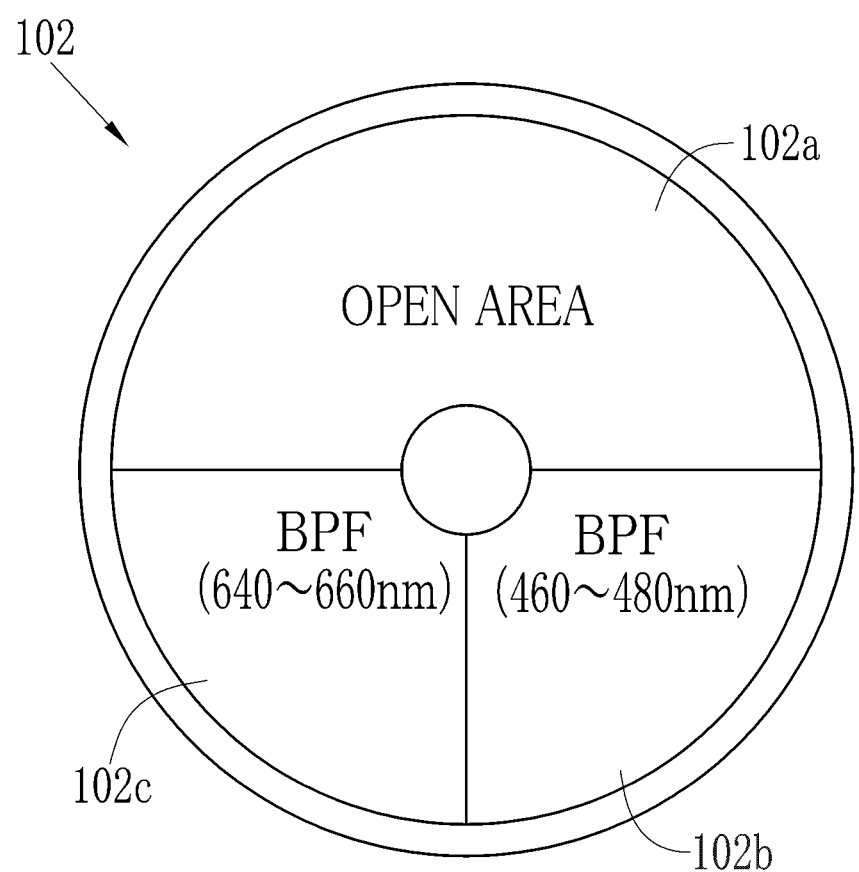
FIG. 19 is a plan illustrating a rotary filter of the second embodiment.

As illustrated in FIG. 19, the rotary filter 102 includes an open area 102a, a BPF (band pass filter) 102b and a BPF (band pass filter) 102c arranged circumferentially, the open area 102a passing the broad band light BB originally, the BPF 102b passing blue narrow band light BN having a center wavelength of 473 nm (wavelength range of 460-480 nm) in the broad band light BB, the BPF 102c passing red narrow band light RN having a center wavelength of 650 nm in the broad band light BB. Thus, the broad band light BB, blue narrow band light BN and red narrow band light RN is sequentially irradiated to the subject body by rotation of the rotary filter 102.

Figure 20A:
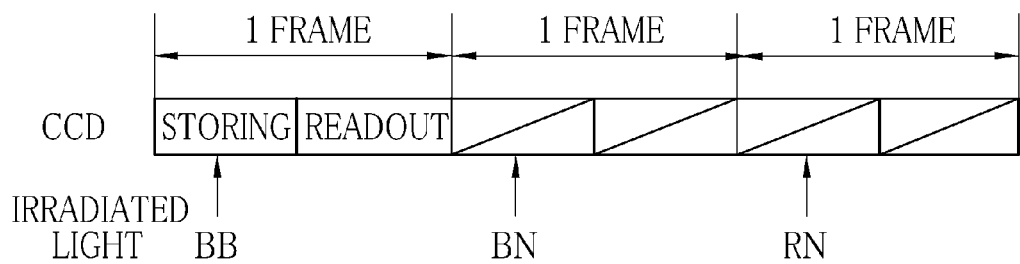
FIG. 20A is an explanatory view illustrating an imaging control of the CCD in the normal imaging mode in the second embodiment.

Image light of the reflected light from the subject body is sequentially imaged by the color CCD 44. As illustrated in FIG. 20A, while the normal imaging mode is set in the imaging control of the CCD 44, the charge storing step and the signal readout step are performed only in case the broad band light BB is irradiated. In case the blue narrow band light BN and red narrow band light RN is irradiated, then the charge storing step and the signal readout step are not performed. In this operation, the blue, green and red signals read out in the signal readout step correspond respectively to Bc, Gc and Rc in the first embodiment.

Figure 20B:
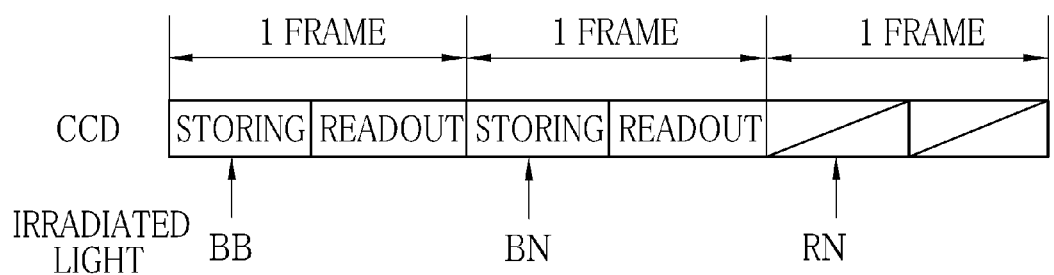
FIG. 20B is an explanatory view illustrating an imaging control of the CCD in the surface imaging mode in the second embodiment.

While the surface imaging mode is set, the charge storing step and signal readout step are carried out only in case the broad band light BB and the blue narrow band light BN is irradiated as illustrated in FIG. 20B, and are not carried out in case the red narrow band light RN is irradiated. In this operation, the blue, green and blue signals read in the signal readout step at the time of irradiating the broad band light BB correspond to respectively Bs1, Gs1 and Rs1 in the first embodiment. The blue, green and blue signals read in the signal readout step at the time of irradiating the blue narrow band light BN correspond to respectively Bs2, Gs2 and Rs2 in the first embodiment.

Figure 20C:
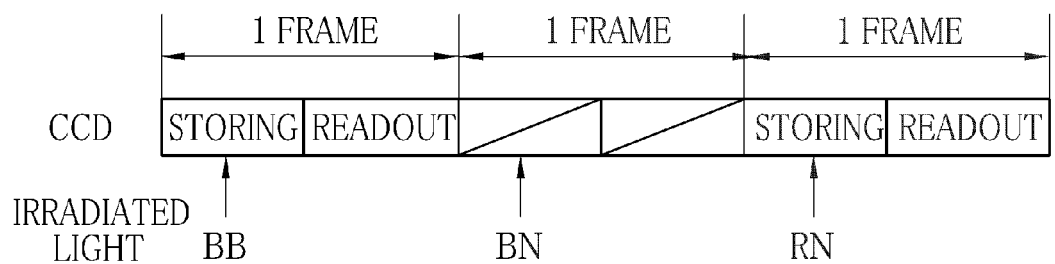
FIG. 20C is an explanatory view illustrating an imaging control of the CCD in the intermediate and deep imaging mode in the second embodiment.

While the intermediate and deep imaging mode is set, the charge storing step and signal readout step are carried out only in case the broad band light BB and the red narrow band light RN is irradiated, and are not carried out in case the blue narrow band light BN is irradiated as illustrated in FIG. 20C. In this operation, the blue, green and red signals read out in the signal readout step at the time of irradiating the broad band light BB correspond to respectively Bd1, Gd1 and Rd1 of the first embodiment. The blue, green and red signals read in the signal readout step at the time of irradiating the red narrow band light RN correspond to respectively Bd2, Gd2 and Rd2 of the first embodiment.

In the third embodiment of the present invention, a first one of the light types of the two wavelengths for use in determining the oxygen saturation level is light from the semiconductor light source similar to the first embodiment. A second one of the light types for use is light separated from the broad band light BB of a white light source such as a xenon lamp by the wavelength separation.

Figure 21:
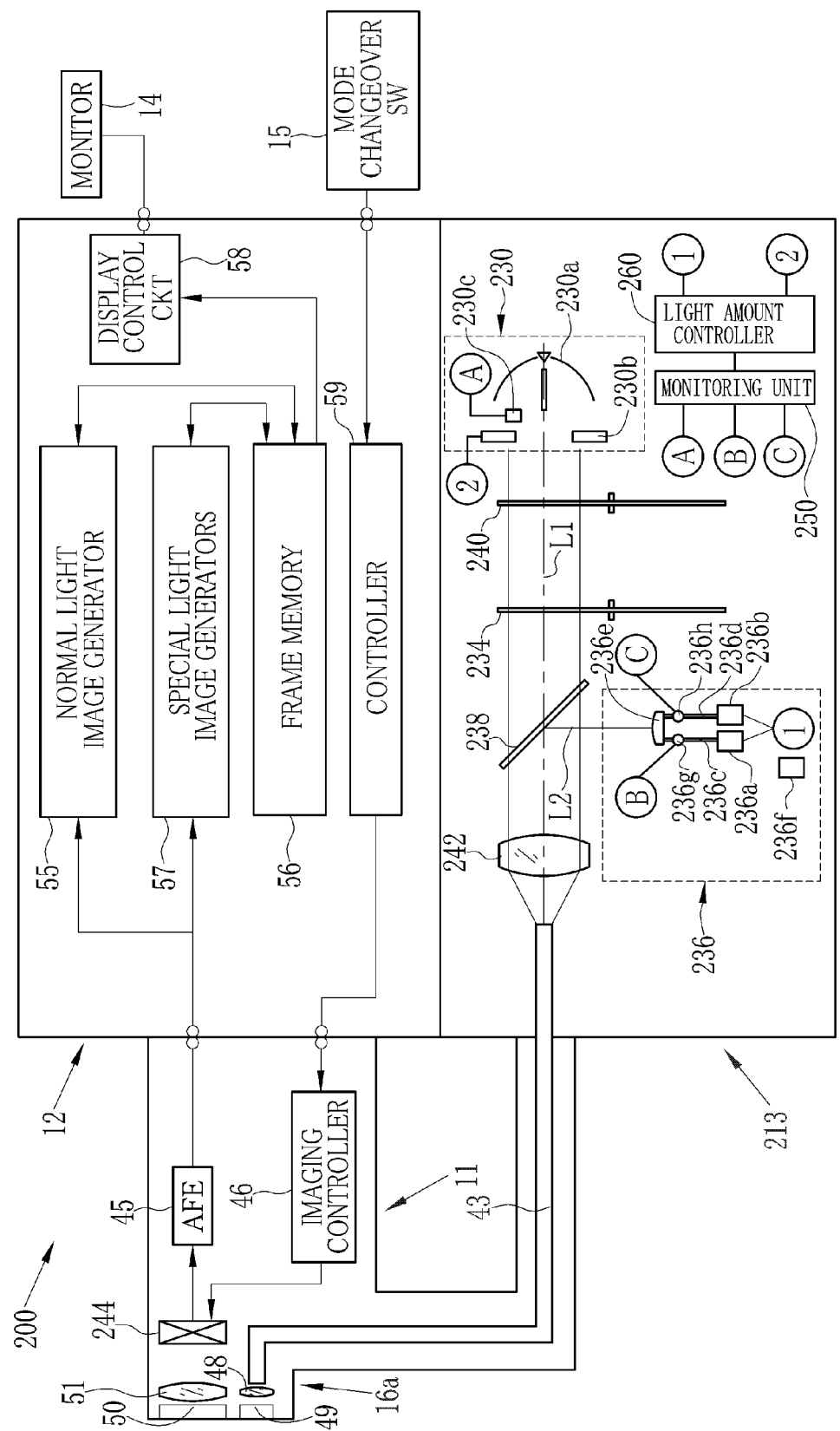
FIG. 21 is a schematic view illustrating an endoscope system of a third embodiment.

As illustrated in FIG. 21, an illuminator 213 in an endoscope system 200 of the third embodiment is structurally different from the illuminator 13 of the first embodiment. A structure of the CCD in the electronic endoscope 11 and operation of the imaging controller 46 are different from those of the first embodiment. However, remaining elements are the same as the first embodiment. Only the elements different from the first embodiments will be hereafter described.

The illuminator 213 includes a white light source 230, a rotary filter 234, a semiconductor light source unit 236, a light coupling device 238 and a shutter plate 240, the white light source 230 emitting broad band light BB (400-700 nm), the rotary filter 234 separating the broad band light BB of the white light source 230 by color separation into three color light of B, G and R, and supplying the three color light to the light guide 43 sequentially, the semiconductor light source unit 236 emitting blue narrow band light EN and red narrow band light RN, the light coupling device 238 combining a light path L2 of the blue narrow band light BN and red narrow band light RN with a light path L1 of the broad band light BB between the rotary filter 234 and the light guide 43, the shutter plate 240 closing a light path of the broad band light BB between the white light source 230 and the rotary filter 234 at a predetermined time point.

The illuminator 213 includes a monitoring unit 250 and a light amount controller 260. The monitoring unit 250 monitors light amounts of the broad band light BB, the blue narrow band light BN and the red narrow band light RN to stabilize the light amounts of those light components for use in acquiring the oxygen saturation level. The light amount controller 260 controls the light amounts according to a result of the light amount monitoring of the monitoring unit 250.

The white light source 230 includes a light source main unit 230a for emitting the broad band light BB, and an aperture stop device 230b for adjusting the light amount of the broad band light BB. The light source main unit 230a is constituted by a xenon lamp, halogen lamp, metal halide lamp or the like. Openness of the aperture stop device 230b is adjusted by the light amount controller 260.

Figure 22:
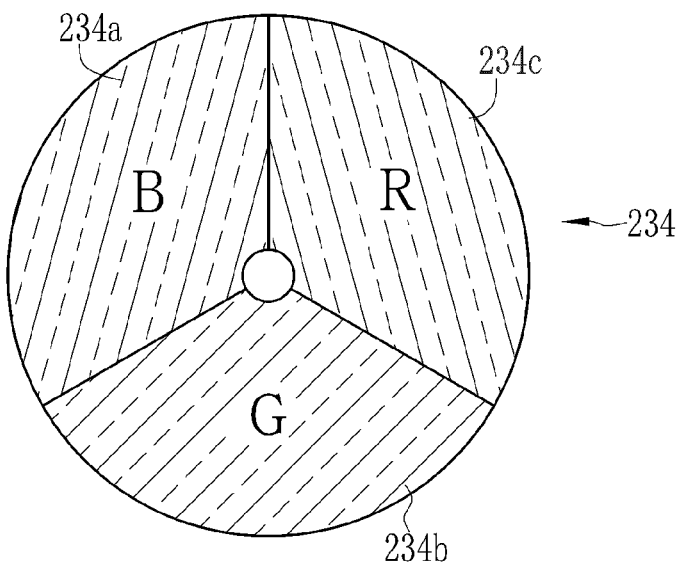
FIG. 22 is a plan illustrating an R, G and B rotary filter.

As illustrated in FIG. 22, the rotary filter 234 is disposed so rotatably that a B filter area 234a, a G filter area 234b and an R filter area 234c are selectively entered in the light path L1 of the broad band light BB. The rotary filter 234 is in a disk shape, where the B filter area 234a, the G filter area 234b and the R filter area 234c are disposed in sector regions with a central angle of 120 degrees by circumferential three-part division of the rotary filter 234.

Figure 23:
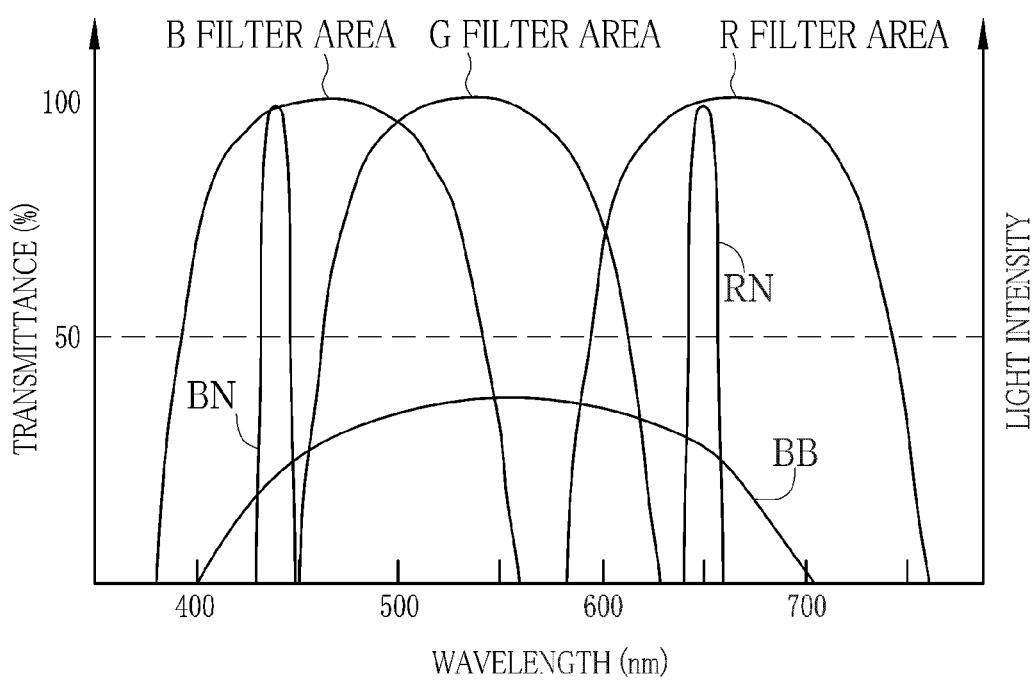
FIG. 23 is a graph illustrating a spectral transmittance of B, G and R filters and emission intensity of broad band light BB, blue narrow band light BN and red narrow band light RN.

As illustrated in FIG. 23, the B filter area 234a passes B light of a blue color range from the broad band light BB. The G filter area 234b passes G light of a green color range from the broad band light BB. The R filter area 234c passes R light of a red color range from the broad band light BB. Thus, B, G and R components of the light are exited sequentially from the rotary filter 234 by its rotation.

The semiconductor light source unit 236 includes first and second laser light sources 236a and 236b, optical fibers 236c and 236d, a coupler 236e and a light source controller 236f. As illustrated in FIG. 23, the first laser light source 236a emits blue narrow band light BN with a center wavelength of 473 nm. The second laser light source 236b emits red narrow band light RN with a center wavelength of 650 nm. The first and second laser light sources 236a and 236b are turned on and off in compliance with control of the light source controller 236f. In the normal imaging mode, both of the first and second laser light sources 236a and 236b are turned off. In the surface imaging mode, only the first laser light source 236a is turned on. In the intermediate and deep imaging mode, only the second laser light source 236b is turned on.

The optical fibers 236c and 236d guide narrow band light from respectively the first and second laser light sources 236a and 236b, and causes this to enter the coupler 236e. The coupler 236e sets the blue and red narrow band light BN and RN from the optical fibers 236c and 236d coaxial with one another at their optical axis. The blue and red narrow band light BN and RN exited from the coupler 236e is directed to the semiconductor light source unit 236 upon passage through a collimator lens (not shown).

The light coupling device 238 is a dichroic mirror, allows passage of light from the rotary filter 234 traveling through the light path L1, but reflects the blue narrow band light BN and the red narrow band light RN from the semiconductor light source unit 236 traveling through the light path L2. The light of the components coupled by the light coupling device 238 enters a condensing lens 242 and becomes incident upon the light guide 43.

Figure 24:
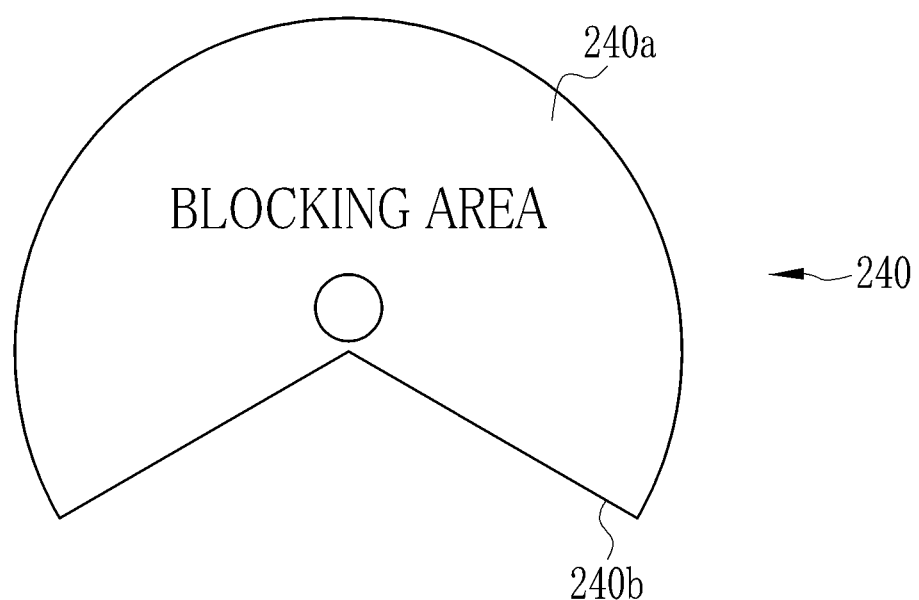
FIG. 24 is a plan illustrating a shutter plate.

As illustrated in FIG. 24, the shutter plate 240 includes a blocking area 240a and an open area 240b, the blocking area 240a having a central angle of 240 degrees and blocking the broad band light BB, the open area 240b having a remaining central angle of 120 degrees and passing the broad band light BB. The shutter plate 240 is kept rotatable, and causes the blocking area 240a and the open area 240b alternately to enter the light path of the broad band light BB selectively.

The rotational movement of the shutter plate 240 is different between the normal imaging mode and the surface imaging mode or intermediate and deep imaging mode. In the normal imaging mode, the shutter plate 240 is stopped by positioning the blocking area 240a away from the light path L1 of the broad band light BB and entering the open area 240b in the light path L1. Thus, the broad band light BB always enters the rotary filter 234. It follows that light of three colors including B, G and R light is sequentially generated according to the type of the B, G and R filter areas 234a, 234b and 234c entered in the light path L1 of the broad band light BB.

On the other hand, in the surface imaging mode or intermediate and deep imaging mode, the shutter plate 240 rotates at the same speed as the rotary filter 234 to set the open area 240b rotationally in phase with the G filter area 234b. Thus, the broad band light BB passes the G filter area 234b to emit G color light while the open area 240b is entered in the light path L1 of the broad band light BB and the blocking area 240a is away from the light path L1. In contrast with this, the broad band light BB is blocked while the blocking area 240a is entered in the light path L1 of the broad band light BB and the open area 240b is away from the light path L1. The first and second laser light sources 236a and 236b are sequentially turned on while the broad band light BB is blocked, to supply the electronic endoscope 11 with the blue and red narrow band light BN and RN.

The monitoring unit 250 monitors light amounts of the broad band light BB, the blue narrow band light BN and the red narrow band light RN according to detection signals from a light amount detector 230c attached to the light source main unit 230a and light amount detectors 236g and 236h attached to the optical fibers 236c and 236d. The monitoring unit 250 monitors to what extent the broad band light BB, the blue narrow band light BN and the red narrow band light RN during the monitoring are different from the light amount of the predetermined standard condition. An amount of the difference in the light amount in the monitoring is sent to the light amount controller 260. The light amount in the standard condition is predetermined prior to the use of the endoscope.

The light amount controller 260 controls the openness of the aperture stop device 230b and driving of the first and second laser light sources 236a and 236b according to a difference in the light amount from the standard condition as detected by the monitoring unit 250. This control of driving adjusts the broad band light BB, blue narrow band light BN and red narrow band light RN at the light amounts of the standard condition. Also, the light amounts of the B, G and R light separated by the rotary filter 234 are adjusted by the light amount adjustment of the broadband light BB.

A CCD 244 in the electronic endoscope is a monochromatic imaging element without a micro color filter on an imaging surface in a manner different from the above-described first and second embodiments. Also, the imaging controller 46 for controlling the imaging of the CCD 244 operates differently from the above-described first and second embodiments.

Figure 25A:
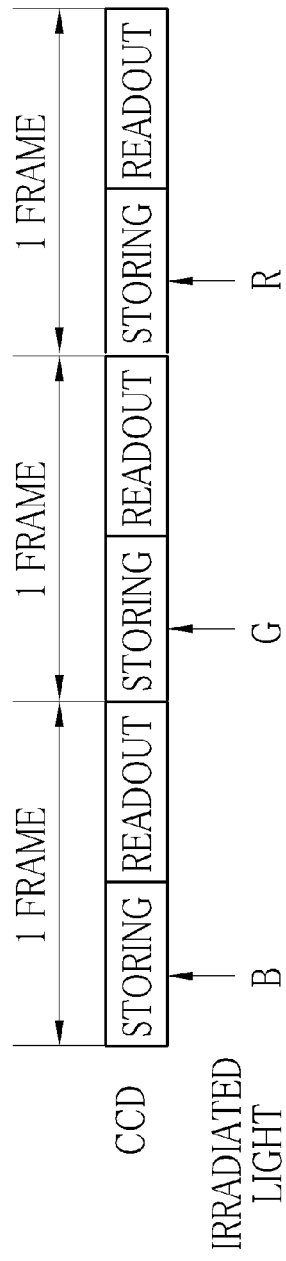
FIG. 25A is an explanatory view illustrating an imaging control of the CCD in the normal imaging mode in the third embodiment.

As illustrated in FIG. 25A, the image light of the three colors B, G and R in the normal imaging mode are sequentially converted photoelectrically to store charge. Frame sequential image signals B, G and R are sequentially output according to the stored charge. Those sequential steps are repeated in a predetermined cycle operation while the normal imaging mode is set. The frame sequential image signals B, G and R correspond respectively to Bc, Gc and Rc of the first embodiment.

Figure 25B:
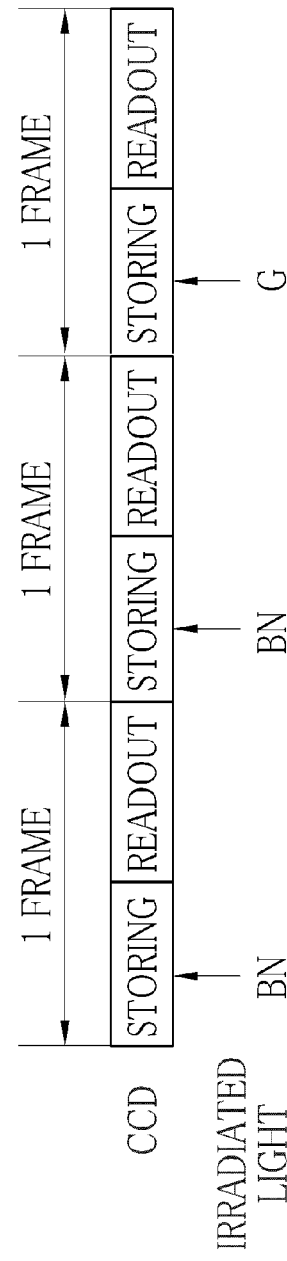
FIG. 25B is an explanatory view illustrating an imaging control of the CCD in the surface imaging mode in the third embodiment.

In the surface imaging mode, image light of the blue narrow band light BN of two frames and image light of the G color of one frame are converted photoelectrically in a sequential manner to store charge, as illustrated in FIG. 25B. According to the stored charge, a frame sequential image signal BN of the two frames and a frame sequential image signal G of one frame are output sequentially. Those steps of the sequential operation are repeated in a predetermined cycle operation while the surface imaging mode is set. The frame sequential image signals BN and G correspond respectively to the signals Bs2 and Gs1 of the first embodiment. It is preferable to process the frame sequential image signal BN of the two frames in the synthesis processing for the purpose of increasing the image quality.

Figure 25C:
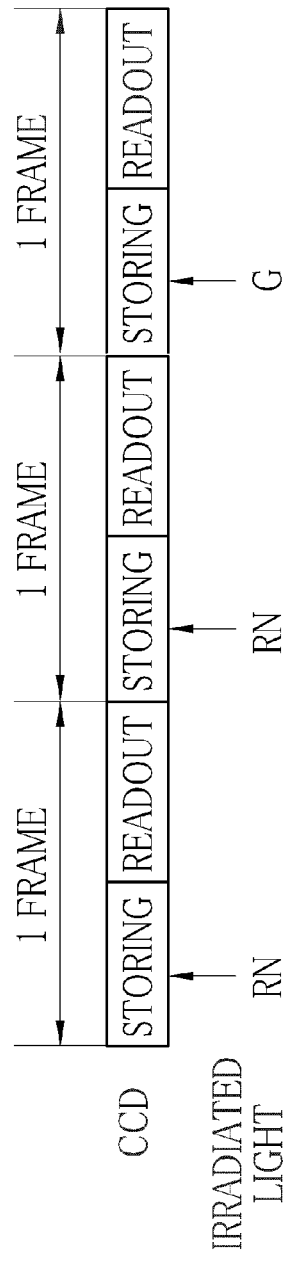
FIG. 25C is an explanatory view illustrating an imaging control of the CCD in the intermediate and deep imaging mode in the third embodiment.

In the intermediate and deep imaging mode, image light of the red narrow band light RN of two frames and image light of the G color of one frame are converted photoelectrically in a sequential manner to store charge, as illustrated in FIG. 25C. According to the stored charge, a frame sequential image signal RN of the two frames and a frame sequential image signal G of one frame are output sequentially. Those steps of the sequential operation are repeated in a predetermined cycle operation while the intermediate and deep imaging mode is set. The frame sequential image signals RN and G correspond respectively to the signals Rd2 and Gd1 of the first embodiment. It is preferable to process the frame sequential image signal RN of the two frames in the synthesis processing for the purpose of increasing the image quality.

In the third embodiment, the G light, blue narrow band light BN and red narrow band light RN for use in determining the oxygen saturation level are adjusted at the light amounts of the standard condition in the illuminator 213. The frame sequential image signals G, BN and RN obtained by imaging the image light of those light components are adjusted at signal values of the standard condition on the assumption of no presence of a lesion or other abnormal part. Therefore, the oxygen saturation level of blood vessels of a particular depth can be determined with good precision, owing to the adjustment at the signal values of the standard condition and generation of normalized signals BN/G and RN/G according to the signal values.

In the above embodiments, the image is expressed locally in the pseudo color only in the low oxygen condition with the oxygen saturation level lower than 60%. However, it is possible instead to express the image in the pseudo color in any of the oxygen saturation levels including the low oxygen condition to the high oxygen condition.

In the first embodiment, the light amounts of the excitation light source 30a, the blue narrow band light source 31 and the red narrow band light source 32 are controlled to set the normalized signal at a signal value of the standard condition. In the third embodiment, the light amount of white light is controlled by adjusting the openness of the aperture stop device 230b, and the light amount of the first or second laser light source is controlled. Instead of those, the normalized signal itself can be adjusted at a signal value of the standard condition according to a result of monitoring the light amounts.

In the above embodiments, the information of the oxygen saturation level is considered in the blood vessel enhanced image in which blood vessels of a predetermined depth are enhanced in the normal light image. However, it is possible alternatively to consider the information of the oxygen saturation level in the normal light image itself.

In the above-described embodiments, the oxygen saturation level is visualized. In place of this or in addition to this, it is possible to visualize an oxyhemoglobin index obtained from the "blood amount (sum of amounts of oxyhemoglobin and deoxyhemoglobin)×oxygen saturation level (%)", or visualize a deoxyhemoglobin index obtained from the "blood amount×(100−oxygen saturation level)".

Although the present invention has been fully described by way of the preferred embodiments thereof with reference to the accompanying drawings, various changes and modifications will be apparent to those having skill in this field. Therefore, unless otherwise these changes and modifications depart from the scope of the present invention, they should be construed as included therein.

What is claimed is:

1. An endoscope system comprising:
an illuminator for irradiating first light having a first wavelength range and having an absorption coefficient changeable with an oxygen saturation level of hemoglobin in blood and second light having a second wavelength range different from said first wavelength range to a subject body;
an imaging element for imaging of a reflection image of said subject body illuminated with said first light and second light, to acquire a first image signal according to reflected light of said first, and to acquire a second image signal according to reflected light of said second light;
a processor configured for:
normalizing said first image signal by use of said second image signal to form a normalized signal;
referring to a first memory which previously stores a relationship between said normalized signal and said oxygen saturation level to generate an oxygen saturation level image by visualizing said oxygen saturation level of a blood vessel present at a particular depth according to said normalized signal and said relationship from said first memory; and
displaying said oxygen saturation level image on a display,
wherein said first image signal includes information of said oxygen saturation level and shape information of said subject body, said second image signal includes shape information of said subject body, and luminance value becomes uniform in portions without said information of said oxygen saturation level in said normalized signal.

2. An endoscope system as defined in claim 1, wherein said illuminator is further configured for irradiating white light to said subject body;
said imaging element acquires a third image signal according to reflected light of said white light by imaging said subject body illuminated with said white light; and
said processor generates a first oxygen saturation level image in which a blood vessel with a lower value of said oxygen saturation level than a reference value is expressed in a pseudo color according to said normalized signal and said third image signal.

3. An endoscope system as defined in claim 2, wherein said processor acquires said oxygen saturation level from said normalized signal according to said relationship from said first memory and generates said first oxygen saturation level image according to said oxygen saturation level and said third image signal.

4. An endoscope system as defined in claim 3, wherein said processor generates a blood vessel enhanced image in which said blood vessel at said particular depth is enhanced according to said third image signal and generates said first oxygen saturation level image based on said oxygen saturation level with said blood vessel enhanced image.

5. An endoscope system as defined in claim 4, wherein said processor is further configured for:

generating a normal light image according to said third image signal;
creating a blood vessel extraction image in which said blood vessel at said particular depth is extracted from said normal light image; and
generating said blood vessel enhanced image by combining said blood vessel extraction image with said normal light image.

6. An endoscope system as defined in claim 5, wherein said processor extracts said blood vessel at said particular depth from said normal light image according to a ratio between blue and green signals in said normal light image.

7. An endoscope system as defined in claim 2, wherein said processor is further configured for:
referring a second memory which previously stores a relationship between said normalized signal and a gain for changing a signal value of said third image signal;
acquiring said gain from said normalized signal according to said relationship from said second memory; and
generating said oxygen saturation level image by changing said signal value of said third image signal according to said gain.

8. An endoscope system as defined in claim 1, wherein said processor generates a second oxygen saturation level image according to said normalized signal in such a form that a blood vessel and a portion different from said blood vessel are expressed in a pseudo color and that a color of said blood vessel is changed according to said oxygen saturation level.

9. An endoscope system as defined in claim 1, further comprising a controller for controlling said illuminator or said imaging element to set a signal ratio between said first and second image signals at a predetermined value.

10. An endoscope system as defined in claim 1, wherein said illuminator includes:
a first semiconductor light source for emitting said first light;
a second semiconductor light source for emitting said second light.

11. An endoscope system as defined in claim 1, wherein said illuminator includes:
a first semiconductor light source for emitting said first light;
a wavelength separator for creating said second light by wavelength separation of white light.

12. An endoscope system as defined in claim 1,
wherein said illuminator irradiates said first light having said first wavelength range of 460-480 nm, and said processor generates an oxygen saturation level image by visualizing said oxygen saturation level of a blood vessel present at a depth of surface tissue, or
wherein said illuminator irradiates said first light having said first wavelength range of 640-660 nm, and said processor generates an oxygen saturation level image by visualizing said oxygen saturation level of a blood vessel present at a depth of intermediate or deep tissue.

13. A processing apparatus for an endoscope system, comprising:
a receiver for receiving first and second image signals from an electronic endoscope, said electronic endoscope including
an illuminator for irradiating first light having a first wavelength range and having an absorption coefficient changeable with an oxygen saturation level of hemoglobin in blood and second light having a second wavelength range different from said first wavelength range to a subject body, and an imaging element for imaging of a reflection image of said subject body illuminated with said first light and second light, to acquire said first image signal according to reflected light of said first light, and to acquire said second image signal according to reflected light of said second light; and
a processor configured for
normalizing said first image signal by use of said second image signal to form a normalized signal;
referring a first memory which previously stores a relationship between said normalized signal and said oxygen saturation level to generate an oxygen saturation level image by visualizing said oxygen saturation level of a blood vessel present at a particular depth according to said normalized signal and said relationship from said first memory,
wherein said first image signal includes information of said oxygen saturation level and shape information of said subject body, said second image signal includes shape information of said subject body, and luminance value becomes uniform in portions without said information of said oxygen saturation level in said normalized signal.

14. An image generating method comprising:
an illuminating step of irradiating first light having a first wavelength range and having an absorption coefficient changeable with an oxygen saturation level of hemoglobin in blood and second light having a second wavelength range different from said first wavelength range to a subject body;
an image signal acquiring step of imaging of a reflection image of said subject body illuminated with said first light and second light, to acquire a first image signal according to reflected light of said first light, and to acquire a second image signal according to reflected light of said second light;
a normalized signal forming step of normalizing said first image signal by use of said second image signal to form a normalized signal;
an oxygen saturation level image generating step of referring a first memory which previously stores a relationship between said normalized signal and said oxygen saturation level to generate an oxygen saturation level image by visualizing said oxygen saturation level of a blood vessel present at a particular depth according to said normalized signal and said relationship from said first memory,
wherein said first image signal includes information of said oxygen saturation level and shape information of said subject body, said second image signal includes shape information of said subject body, and luminance value becomes uniform in portions without said information of said oxygen saturation level in said normalized signal.

* * * * *